United States Patent
Qu et al.

(10) Patent No.: US 10,905,743 B2
(45) Date of Patent: Feb. 2, 2021

(54) INTERLEUKIN 15 PROTEIN COMPLEX

(71) Applicants: Jiangsu Hengrui Medicine Co., Ltd., Jiangsu (CN); Shanghai Hengrui Pharmaceutical Co., Ltd., Shanghai (CN)

(72) Inventors: Xiangdong Qu, Shanghai (CN); Xin Ye, Shanghai (CN); Qiyue Hu, Shanghai (CN); Dongbing Cui, Shanghai (CN); Weikang Tao, Shanghai (CN); Lianshan Zhang, Shanghai (CN); Piaoyang Sun, Jiangsu (CN)

(73) Assignees: Jiangsu Hengrui Medicine Co., Ltd.; Shanghai Hengrui Pharmaceutical Co., Ltd.

( * ) Notice: Subject to any disclaimer, the term of this patent is extended or adjusted under 35 U.S.C. 154(b) by 366 days.

(21) Appl. No.: 15/537,107

(22) PCT Filed: Nov. 17, 2015

(86) PCT No.: PCT/CN2015/094780
§ 371 (c)(1),
(2) Date: Aug. 20, 2018

(87) PCT Pub. No.: WO2016/095642
PCT Pub. Date: Jun. 23, 2016

(65) Prior Publication Data
US 2019/0070264 A1    Mar. 7, 2019

(30) Foreign Application Priority Data

Dec. 19, 2014 (CN) .......................... 2014 1 0799889

(51) Int. Cl.
| | |
|---|---|
| *A61K 38/20* | (2006.01) |
| *C07K 14/54* | (2006.01) |
| *A61P 35/00* | (2006.01) |
| *C07K 14/715* | (2006.01) |
| *C07K 19/00* | (2006.01) |
| *A61P 37/04* | (2006.01) |
| *A61P 37/02* | (2006.01) |
| *A61P 31/00* | (2006.01) |
| *A61P 17/00* | (2006.01) |
| *A61P 19/02* | (2006.01) |
| *A61P 1/00* | (2006.01) |
| *A61P 29/00* | (2006.01) |
| *C12N 15/62* | (2006.01) |
| *A61K 47/64* | (2017.01) |
| *C07K 16/30* | (2006.01) |

(52) U.S. Cl.
CPC .......... *A61K 38/2086* (2013.01); *A61K 38/20* (2013.01); *A61P 1/00* (2018.01); *A61P 17/00* (2018.01); *A61P 19/02* (2018.01); *A61P 29/00* (2018.01); *A61P 31/00* (2018.01); *A61P 35/00* (2018.01); *A61P 37/02* (2018.01); *A61P 37/04* (2018.01); *C07K 14/5443* (2013.01); *C07K 14/7155* (2013.01); *C07K 19/00* (2013.01); *C12N 15/62* (2013.01); *A61K 47/642* (2017.08); *A61K 2300/00* (2013.01); *C07K 16/30* (2013.01); *C07K 2319/30* (2013.01)

(58) Field of Classification Search
CPC ................................................ A61K 38/2086
See application file for complete search history.

(56) References Cited

U.S. PATENT DOCUMENTS 10,206,980 B2 *   2/2019   Qu .................... A61K 38/1793

FOREIGN PATENT DOCUMENTS

| | | |
|---|---|---|
| CN | 1760209 A | 4/2006 |
| CN | 103370339 A | 10/2013 |
| CN | 104093841 A | 10/2014 |
| WO | 2012/040323 A2 | 3/2012 |
| WO | 2012/175222 A1 | 12/2012 |
| WO | 2014022592 A1 | 2/2014 |

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990), pp. 126-128 and 228-234.*
Int'l Search Report dated Feb. 17, 2016 in Int'l Application No. PCT/CN2015/094780.

* cited by examiner

Primary Examiner — Prema M Mertz
(74) Attorney, Agent, or Firm — Ice Miller LLP

(57) ABSTRACT

An interleukin 15 (IL-15) protein complex is provided. The IL-15 protein complex includes soluble fusion proteins (I) and (II), wherein the fusion protein (I) is an IL-15 polypeptide or a functional fragment thereof, and the soluble fusion protein (II) is an IL-15Rα polypeptide or a functional fragment thereof. The soluble fusion protein (I) has at least one amino acid residue mutated to a cysteine (Cys) residue, which pairs with a corresponding mutated Cys residue on the soluble fusion protein (II), or vice versa, to form one or more disulfide bonds. The IL-15 protein complex can be used for tumor therapy.

10 Claims, 5 Drawing Sheets
Specification includes a Sequence Listing.

```
                        SEQUENCE LISTING

<160> NUMBER OF SEQ ID NOS: 20

<210> SEQ ID NO 1
<211> LENGTH: 114
<212> TYPE: PRT
<213> ORGANISM: HOMO SAPIENS

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 114
<212> TYPE: PRT
<213> ORGANISM: ARTIFICIAL
<220> FEATURE:
<223> OTHER INFORMATION: IL-15(L52C)

<400> SEQUENCE: 2

Asn Trp Val Asn Val Ile Ser Asp Leu Lys Lys Ile Glu Asp Leu Ile
1               5                   10                  15
```

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Cys Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 3
<211> LENGTH: 175
<212> TYPE: PRT
<213> ORGANISM: ARTIFICIAL
<220> FEATURE:
<223> OTHER INFORMATION: IL-15R alpha-ECD

<400> SEQUENCE: 3

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 4
<211> LENGTH: 73
<212> TYPE: PRT
<213> ORGANISM: ARTIFICIAL
<220> FEATURE:
<223> OTHER INFORMATION: IL-15R alpha-sushi+

<400> SEQUENCE: 4

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30
```

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
 50                  55                  60

Arg Asp Pro Ala Leu Val His Gln Arg
 65                  70

<210> SEQ ID NO 5
<211> LENGTH: 417
<212> TYPE: PRT
<213> ORGANISM: ARTIFICIAL
<220> FEATURE:
<223> OTHER INFORMATION: IL-15R alpha-ECD(S40C)-Fc

<400> SEQUENCE: 5

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
        35                  40                  45

Lys Ala Thr Asn Val Ala His Trp Thr Thr Pro Ser Leu Lys Cys Ile
 50                  55                  60

Arg Asp Pro Ala Leu Val His Gln Arg Pro Ala Pro Ser Thr Val
 65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Gly
                165                 170                 175

Gly Gly Gly Ser Gly Gly Gly Gly Ser Glu Pro Lys Ser Ser Asp Lys
            180                 185                 190

Thr His Thr Cys Pro Pro Cys Pro Ala Pro Glu Leu Leu Gly Gly Pro
        195                 200                 205

Ser Val Phe Leu Phe Pro Pro Lys Pro Lys Asp Thr Leu Met Ile Ser
210                 215                 220

Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
            260                 265                 270

Val Ser Val Leu Thr Val Leu His Gln Asp Trp Leu Asn Gly Lys Glu
        275                 280                 285

Tyr Lys Cys Lys Val Ser Asn Lys Ala Leu Pro Ala Pro Ile Glu Lys
290                 295                 300

Thr Ile Ser Lys Ala Lys Gly Gln Pro Arg Glu Pro Gln Val Tyr Thr
305                 310                 315                 320

```
Leu Pro Pro Ser Arg Glu Glu Met Thr Lys Asn Gln Val Ser Leu Thr
            325                 330                 335

Cys Leu Val Lys Gly Phe Tyr Pro Ser Asp Ile Ala Val Glu Trp Glu
            340                 345                 350

Ser Asn Gly Gln Pro Glu Asn Asn Tyr Lys Thr Thr Pro Pro Val Leu
            355                 360                 365

Asp Ser Asp Gly Ser Phe Phe Leu Tyr Ser Lys Leu Thr Val Asp Lys
        370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys

<210> SEQ ID NO 6
<211> LENGTH: 417
<212> TYPE: PRT
<213> ORGANISM: ARTIFICIAL
<220> FEATURE:
<223> OTHER INFORMATION: Fc-IL-15R alpha-ECD(S40C)

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys Gly Gly Gly Ser Gly Gly Gly
225                 230                 235                 240

Gly Ser Ile Thr Cys Pro Pro Pro Met Ser Val Glu His Ala Asp Ile
                245                 250                 255

Trp Val Lys Ser Tyr Ser Leu Tyr Ser Arg Glu Arg Tyr Ile Cys Asn
```

```
              260                 265                 270
    Ser Gly Phe Lys Arg Lys Ala Gly Thr Cys Ser Leu Thr Glu Cys Val
                275                 280                 285

Leu Asn Lys Ala Thr Asn Val Ala His Trp Thr Thr Pro Ser Leu Lys
                290                 295                 300

Cys Ile Arg Asp Pro Ala Leu Val His Gln Arg Pro Ala Pro Pro Ser
    305                 310                 315                 320

Thr Val Thr Thr Ala Gly Val Thr Pro Gln Pro Glu Ser Leu Ser Pro
                    325                 330                 335

Ser Gly Lys Glu Pro Ala Ala Ser Ser Pro Ser Ser Asn Asn Thr Ala
                    340                 345                 350

Ala Thr Thr Ala Ala Ile Val Pro Gly Ser Gln Leu Met Pro Ser Lys
                    355                 360                 365

Ser Pro Ser Thr Gly Thr Thr Glu Ile Ser Ser His Glu Ser Ser His
                    370                 375                 380

Gly Thr Pro Ser Gln Thr Thr Ala Lys Asn Trp Glu Leu Thr Ala Ser
    385                 390                 395                 400

Ala Ser His Gln Pro Pro Gly Val Tyr Pro Gln Gly His Ser Asp Thr
                    405                 410                 415

Thr

<210> SEQ ID NO 7
<211> LENGTH: 315
<212> TYPE: PRT
<213> ORGANISM: ARTIFICIAL
<220> FEATURE:
<223> OTHER INFORMATION: IL-15R alpha-(Sushi+,S40C)-Fc

<400> SEQUENCE: 7

Ile Thr Cys Pro Pro Pro Met Ser Val Glu His Ala Asp Ile Trp Val
    1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Cys Ser Leu Thr Glu Cys Val Leu Asn
                35                  40                  45

Lys Ala Thr Asn Val Ala His Trp Thr Thr Pro Ser Leu Lys Cys Ile
                50                  55                  60

Arg Asp Pro Ala Leu Val His Gln Arg Gly Gly Gly Ser Gly Gly
    65                  70                  75                  80

Gly Gly Ser Glu Pro Lys Ser Ser Asp Lys Thr His Thr Cys Pro Pro
                    85                  90                  95

Cys Pro Ala Pro Glu Leu Leu Gly Gly Pro Ser Val Phe Leu Phe Pro
                    100                 105                 110

Pro Lys Pro Lys Asp Thr Leu Met Ile Ser Arg Thr Pro Glu Val Thr
                    115                 120                 125

Cys Val Val Val Asp Val Ser His Glu Asp Pro Glu Val Lys Phe Asn
    130                 135                 140

Trp Tyr Val Asp Gly Val Glu Val His Asn Ala Lys Thr Lys Pro Arg
    145                 150                 155                 160

Glu Glu Gln Tyr Asn Ser Thr Tyr Arg Val Val Ser Val Leu Thr Val
                    165                 170                 175

Leu His Gln Asp Trp Leu Asn Gly Lys Glu Tyr Lys Cys Lys Val Ser
                    180                 185                 190

Asn Lys Ala Leu Pro Ala Pro Ile Glu Lys Thr Ile Ser Lys Ala Lys
                    195                 200                 205
```

```
Gly Gln Pro Arg Glu Pro Gln Val Tyr Thr Leu Pro Pro Ser Arg Glu
        210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
            260                 265                 270

Phe Leu Tyr Ser Lys Leu Thr Val Asp Lys Ser Arg Trp Gln Gln Gly
        275                 280                 285

Asn Val Phe Ser Cys Ser Val Met His Glu Ala Leu His Asn His Tyr
    290                 295                 300

Thr Gln Lys Ser Leu Ser Leu Ser Pro Gly Lys
305                 310                 315

<210> SEQ ID NO 8
<211> LENGTH: 315
<212> TYPE: PRT
<213> ORGANISM: ARTIFICIAL
<220> FEATURE:
<223> OTHER INFORMATION: Fc-IL-15R alpha-sushi+(S40C)

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Ile Thr Cys Pro Pro Pro Met Ser Val Glu His Ala Asp Ile
                245                 250                 255
```

```
Trp Val Lys Ser Tyr Ser Leu Tyr Ser Arg Glu Arg Tyr Ile Cys Asn
        260                 265                 270

Ser Gly Phe Lys Arg Lys Ala Gly Thr Cys Ser Leu Thr Glu Cys Val
        275                 280                 285

Leu Asn Lys Ala Thr Asn Val Ala His Trp Thr Thr Pro Ser Leu Lys
        290                 295                 300

Cys Ile Arg Asp Pro Ala Leu Val His Gln Arg
305                 310                 315

<210> SEQ ID NO 9
<211> LENGTH: 232
<212> TYPE: PRT
<213> ORGANISM: ARTIFICIAL
<220> FEATURE:
<223> OTHER INFORMATION: Fc fragment, IgG1-Fc

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 10
<211> LENGTH: 411
<212> TYPE: DNA
<213> ORGANISM: HOMO SAPIENS

<400> SEQUENCE: 10

```
atggacatgc gggtgccagc ccagctgctg ggcctgttgc tgctgtggtt ccccggctct      60
cggtgcaact gggtgaatgt aattagtgat ttgaaaaaaa ttgaagatct tattcaatct     120
atgcatattg atgctacttt atatacggaa agtgatgttc acccgagttg caaagtaaca     180
gcaatgaagt gctttctctt ggagttacaa gttatttcac ttgagtccgg cgatgcaagt     240
attcatgata cagtagaaaa tctgatcatc ttagcaaaca acagtttgtc ttctaatggg     300
aatgtaacag aatctggatg caaagaatgt gaggaactgg aggaaaaaaa tattaaagaa     360
tttttgcaga gttttgtaca tattgtccaa atgttcatca acacttcttg a              411
```

<210> SEQ ID NO 11
<211> LENGTH: 1320
<212> TYPE: DNA
<213> ORGANISM: ARTIFICIAL
<220> FEATURE:
<223> OTHER INFORMATION: IL-15R alpha-ECD-Fc vector sequence

<400> SEQUENCE: 11

```
atggacatgc gggtgccagc ccagctgctg ggcctgttgc tgctgtggtt ccccggctct      60
cggtgcatca cctgccctcc acctatgtcc gtggaacacg cagacatctg ggtcaagagc     120
tacagcttgt actcccgcga gcgctacatt tgtaactctg gtttcaagcg taaagccggc     180
acctccagcc tgaccgagtg cgtgttgaac aaggccacca atgtcgccca ctggacaacc     240
ccaagtctca atgcattcg cgaccctgcc ctggttcacc aacgcccagc gccaccatcc     300
acagtaacca ctgcaggcgt gaccccacag ccagagagcc tctcccttc tggcaaagag     360
ccagcagctt catctccaag ctcaaacaac acagcggcca acagcagc tattgtcccg      420
ggctcccagc tgatgccttc aaaatcacct tccacaggca ccacagagat cagcagtcat     480
gagtcctccc acggcacccc atctcagaca acagccaaga ctgggaact cacagcatcc     540
gcctcccacc agccgccagg tgtgtatcca cagggccaca gcgacaccac tggcggagga     600
ggctctgggg gcgaggaag cgaacctaag tcctctgata gacccacac atgtcccccc      660
tgcccagctc ctgagctctt gggcggacct tccgtgtttc tgttcccccc aaagcccaag     720
gatacccttata tgatcagcag aacacccgaa gttacttgcg tggtcgtgga cgtttctcac     780
gaagatcctg aagtgaaatt caactggtac gtggatggcg tggaggtgca caatgctaag     840
actaagcccc gtgaagagca gtacaactct acctaccggg tcgtttcagt gctgactgtt     900
ctccatcagg actggctcaa cggaaggag tataagtgca aggtgtctaa caaggcactg     960
cccgcaccca tcgagaagac catttctaag gccaagggtc aaccacggga gccacaggtt     1020
tacacattgc ctcccagtcg ggaggagatg acaaagaatc aagtgtcact acatgtcttc     1080
gtgaagggct ctacccctc agacatcgcc gtggagtggg agagcaacgg acaaccagaa     1140
aacaactaca gaccacacc tcctgtgctc gattcagatg gttcctttttc cttgtacagc     1200
aaactcaccg ttgacaagag tcggtggcag caaggaaatg tgttcagctg ttctgtgatg     1260
cacgaggccc tgcacaacca ttatacccaa aaatctctca gcctttctcc cggcaagtga     1320
```

<210> SEQ ID NO 12

<211> LENGTH: 1350
<212> TYPE: DNA
<213> ORGANISM: ARTIFICIAL
<220> FEATURE:
<223> OTHER INFORMATION: Fc-IL-15R alpha-ECD vector sequence

<400> SEQUENCE: 12

| | | | | | |
|---|---|---|---|---|---|
| atggacatgc | gggtgccagc | ccagctgctg | ggcctgttgc | tgctgtggtt | ccccggctct | 60 |
| cggtgcgaac | ctaagtcctc | tgataagacc | cacacatgtc | cccctgccc | agctcctgag | 120 |
| ctcttgggcg | gaccttccgt | gtttctgttc | cccccaaagc | caaggatac | ccttatgatc | 180 |
| agcagaacac | ccgaagttac | ttgcgtggtc | gtggacgttt | ctcacgaaga | tcctgaagtg | 240 |
| aaattcaact | ggtacgtgga | tggcgtggag | gtgcacaatg | ctaagactaa | gccccgtgaa | 300 |
| gagcagtaca | actctaccta | ccgggtcgtt | tcagtgctga | ctgttctcca | tcaggactgg | 360 |
| ctcaacggga | aggagtataa | gtgcaaggtg | tctaacaagg | cactgccgc | acccatcgag | 420 |
| aagaccattt | ctaaggccaa | gggtcaacca | cgggagccac | aggtttacac | attgcctccc | 480 |
| agtcgggagg | agatgacaaa | gaatcaagtg | tcacttacat | gtcttgtgaa | gggcttctac | 540 |
| ccctcagaca | tcgccgtgga | gtgggagagc | aacggacaac | agaaaacaa | ctacaagacc | 600 |
| acacctcctg | tgctcgattc | agatggttcc | ttttcttgt | acagcaaact | caccgttgac | 660 |
| aagagtcggt | ggcagcaagg | aaatgtgttc | agctgttctg | tgatgcacga | ggccctgcac | 720 |
| aaccattata | cccaaaaatc | tctcagcctt | tctcccggca | agggcggagg | aggctctggc | 780 |
| ggtggtggca | gtggtggcgg | agggtcagga | ggtggtggaa | gcatcacctg | ccctccacct | 840 |
| atgtccgtgg | aacacgcaga | catctgggtc | aagagctaca | gcttgtactc | ccgcgagcgc | 900 |
| tacatttgta | actctggttt | caagcgtaaa | gccggcacct | ccagcctgac | cgagtgcgtg | 960 |
| ttgaacaagg | ccaccaatgt | cgcccactgg | acaaccccaa | gtctcaaatg | cattcgcgac | 1020 |
| cctgccctgg | ttcaccaacg | cccagcgcca | ccatccacag | taaccactgc | aggcgtgacc | 1080 |
| ccacagccag | agagcctctc | cccttctggc | aaagagccag | cagcttcatc | tccaagctca | 1140 |
| aacaacacag | cggccacaac | agcagctatt | gtcccgggct | cccagctgat | gccttcaaaa | 1200 |
| tcaccttcca | caggcaccac | agagatcagc | agtcatgagt | cctcccacgg | cacccatct | 1260 |
| cagacaacag | ccaagaactg | ggaactcaca | gcatccgcct | ccaccagcc | gccaggtgtg | 1320 |
| tatccacagg | gccacagcga | caccacttga | | | | 1350 |

<210> SEQ ID NO 13
<211> LENGTH: 1015
<212> TYPE: DNA
<213> ORGANISM: ARTIFICIAL
<220> FEATURE:
<223> OTHER INFORMATION: IL-15R alpha-shushi+(73)-Fc vector sequence

<400> SEQUENCE: 13

| | | | | | |
|---|---|---|---|---|---|
| atggacatgc | gggtgccagc | ccagctgctg | ggcctgttgc | tgctgtggtt | ccccggctct | 60 |
| cggtgcatca | cctgccctcc | acctatgtcc | gtggaacacg | cagacatctg | gtcaagagc | 120 |
| tacagcttgt | actcccgcga | gcgctacatt | tgtaactctg | gtttcaagcg | taaagccggc | 180 |
| acctccagcc | tgaccgagtg | cgtgttgaac | aaggccacca | atgtcgccca | ctggacaacc | 240 |
| ccaagtctca | aatgcattcg | cgaccctgcc | ctggttcacc | aacgcggcgg | aggaggctct | 300 |
| gggggcggag | gaagcgaacc | taagtcctct | gataagaccc | acacatgtcc | ccctgccca | 360 |
| gctcctgagc | tcttgggcgg | accttccgtg | tttctgttcc | ccccaaagcc | caaggatacc | 420 |
| cttatgatca | gcagaacacc | cgaagttact | tgcgtggtcg | tggacgtttc | tcacgaagat | 480 |

```
cctgaagtga aattcaactg gtacgtggat ggcgtggagg tgcacaatgc taagactaag    540
ccccgtgaag agcagtacaa ctctacctac cgggtcgttt cagtgctgac tgttctccat    600
caggactggc tcaacgggaa ggagtataag tgcaaggtgt ctaacaaggc actgcccgca    660
cccatcgaga agaccatttc taaggccaag ggtcaaccac gggagccaca ggtttacaca    720
ttgcctccca gtcggaggga gatgacaaag aatcaagtgt cacttacatg tcttgtgaag    780
ggcttctacc cctcagacat cgccgtggag tgggagagca acggacaacc agaaaacaac    840
tacaagacca cacctcctgt gctcgattca gatggttcct tttcttgta cagcaaactc    900 accgttgaca gagtcggtg gcagcaagga aatgtgttca gctgttctgt gatgcacgag    960
gccctgcaca accattatac ccaaaaatct ctcagccttt ctcccggcaa gtgac         1015
```

<210> SEQ ID NO 14
<211> LENGTH: 1044
<212> TYPE: DNA
<213> ORGANISM: ARTIFICIAL
<220> FEATURE:
<223> OTHER INFORMATION: Fc-IL-15R alpha-shushi+(73)vector sequence

<400> SEQUENCE: 14

```
atggacatgc gggtgccagc ccagctgctg ggcctgttgc tgctgtggtt ccccggctct    60
cggtgcgaac ctaagtcctc tgataagacc cacacatgtc cccctgccc agctcctgag    120 ctcttgggcg gaccttccgt gtttctgttc ccccaaagc ccaaggatac ccttatgatc    180
agcagaacac ccgaagttac ttgcgtggtc gtggacgttt ctcacgaaga tcctgaagtg    240
aaattcaact ggtacgtgga tggcgtggag gtgcacaatg ctaagactaa gccccgtgaa    300
gagcagtaca actctaccta ccgggtcgtt tcagtgctga ctgttctcca tcaggactgg    360
ctcaacggga aggagtataa gtgcaaggtg tctaacaagg cactgcccgc acccatcgag    420
aagaccattt ctaaggccaa gggtcaacca cgggagccac aggtttacac attgcctccc    480
agtcgggagg agatgacaaa gaatcaagtg tcacttacat gtcttgtgaa gggcttctac    540
ccctcagaca tcgccgtgga gtgggagagc aacggacaac cagaaaacaa ctacaagacc    600
acacctcctg tgctcgattc agatggttcc ttttcttgt acagcaaact caccgttgac    660
aagagtcggt ggcagcaagg aaatgtgttc agctgttctg tgatgcacga ggccctgcac    720
aaccattata cccaaaaatc tctcagcctt tctcccggca agggcggagg aggctctggc    780
ggtggtggca gtggtggcgg agggtcagga ggtggtggaa gcatcacctg ccctccacct    840
atgtccgtgg aacacgcaga catctgggtc aagagctaca gcttgtactc ccgcgagcgc    900
tacatttgta actctggttt caagcgtaaa gccggcacct ccagcctgac cgagtgcgtg    960
ttgaacaagg ccaccaatgt cgcccactgg acaaccccaa gtctcaaatg cattcgcgac    1020
cctgccctgg ttcaccaacg ctga                                           1044
```

<210> SEQ ID NO 15
<211> LENGTH: 411
<212> TYPE: DNA
<213> ORGANISM: ARTIFICIAL
<220> FEATURE:
<223> OTHER INFORMATION: IL-15(L52C)vector sequence

<400> SEQUENCE: 15

```
atggacatgc gggtgccagc ccagctgctg ggcctgttgc tgctgtggtt ccccggctct    60
cggtgcaact gggtgaatgt aattagtgat ttgaaaaaaa ttgaagatct tattcaatct    120
```

| atgcatattg atgctacttt atatacggaa agtgatgttc acccgagttg caaagtaaca | 180 |
| gcaatgaagt gctttctctt ggagttacaa gttatttcat gtgagtccgg cgatgcaagt | 240 |
| attcatgata cagtagaaaa tctgatcatc ttagcaaaca acagtttgtc ttctaatggg | 300 |
| aatgtaacag aatctggatg caaagaatgt gaggaactgg aggaaaaaaa tattaaagaa | 360 |
| tttttgcaga gttttgtaca tattgtccaa atgttcatca acacttcttg a | 411 |

```
<210> SEQ ID NO 16
<211> LENGTH: 1320
<212> TYPE: DNA
<213> ORGANISM: ARTIFICIAL
<220> FEATURE:
<223> OTHER INFORMATION: IL-15R alpha-ECD(S40C)-Fc vector sequence

<400> SEQUENCE: 16
```

| atggacatgc gggtgccagc ccagctgctg ggcctgttgc tgctgtggtt ccccggctct | 60 |
| cggtgcatca cctgccctcc acctatgtcc gtggaacacg cagacatctg ggtcaagagc | 120 |
| tacagcttgt actcccgcga gcgctacatt tgtaactctg gtttcaagcg taaagccggc | 180 |
| acctgcagcc tgaccgagtg cgtgttgaac aaggccacca tgtcgcccca ctggacaacc | 240 |
| ccaagtctca aatgcattcg cgaccctgcc ctggttcacc aacgcccagc gccaccatcc | 300 |
| acagtaacca ctgcaggcgt gaccccacag ccagagagcc tctccccttc tggcaaagag | 360 |
| ccagcagctt catctccaag ctcaaacaac acagcggcca aacagcagc tattgtcccg | 420 |
| ggctcccagc tgatgccttc aaaatcacct tccacaggca ccacagagat cagcagtcat | 480 |
| gagtcctccc acggcacccc atctcagaca acagccaaga ctgggaact cacagcatcc | 540 |
| gcctcccacc agccgccagg tgtgtatcca cagggcacag cgacaccac tggcggagga | 600 |
| ggctctgggg gcggaggaag cgaacctaag tcctctgata gacccacac atgtccccc | 660 |
| tgcccagctc ctgagctctt ggcggacct tccgtgtttc tgttccccc aaagcccaag | 720 |
| gatacccta tgatcagcag aacacccgaa gttacttgcg tggtcgtgga cgtttctcac | 780 |
| gaagatcctg aagtgaaatt caactggtac gtggatggcg tggaggtgca caatgctaag | 840 |
| actaagcccc gtgaagagca gtacaactct acctaccggg tcgtttcagt gctgactgtt | 900 |
| ctccatcagg actggctcaa cgggaaggag tataagtgca aggtgtctaa caaggcactg | 960 |
| cccgcaccca tcgagaagac catttctaag gccaagggtc aaccacggga gccacaggtt | 1020 |
| tacacattgc ctcccagtcg ggaggagatg acaaagaatc aagtgtcact acatgtctt | 1080 |
| gtgaagggct tctaccctc agacatcgcc gtggagtggg agagcaacgg acaaccagaa | 1140 |
| aacaactaca agaccacacc tcctgtgctc gattcagatg gttcctttt cttgtacagc | 1200 |
| aaactcaccg ttgacaagag tcggtggcag caaggaaatg tgttcagctg ttctgtgatg | 1260 |
| cacgaggccc tgcacaacca ttatacccaa aaatctctca gcctttctcc cggcaagtga | 1320 |

```
<210> SEQ ID NO 17
<211> LENGTH: 1350
<212> TYPE: DNA
<213> ORGANISM: ARTIFICIAL
<220> FEATURE:
<223> OTHER INFORMATION: Fc-IL-15R alpha-ECD(S40C)vector sequence
```

<400> SEQUENCE: 17

```
atggacatgc gggtgccagc ccagctgctg ggcctgttgc tgctgtggtt ccccggctct      60
cggtgcgaac ctaagtcctc tgataagacc cacacatgtc cccctgccc agctcctgag     120
ctcttgggcg gaccttccgt gtttctgttc cccccaaagc caaggatac ccttatgatc     180
agcagaacac ccgaagttac ttgcgtggtc gtggacgttt ctcacgaaga tcctgaagtg     240
aaattcaact ggtacgtgga tggcgtggag gtgcacaatg ctaagactaa gccccgtgaa     300
gagcagtaca actctaccta ccgggtcgtt tcagtgctga ctgttctcca tcaggactgg     360
ctcaacggga aggagtataa gtgcaaggtg tctaacaagg cactgcccgc acccatcgag     420
aagaccattt ctaaggccaa gggtcaacca cgggagccac aggtttacac attgcctccc     480
agtcgggagg agatgacaaa gaatcaagtg tcacttacat gtcttgtgaa gggcttctac     540
ccctcagaca tcgccgtgga gtgggagagc aacggacaac agaaaacaa ctacaagacc     600
acacctcctg tgctcgattc agatggttcc ttttcttgt acagcaaact caccgttgac     660
aagagtcggt ggcagcaagg aaatgtgttc agctgttctg tgatgcacga ggccctgcac     720
aaccattata cccaaaaatc tctcagcctt ctcccggca agggcggagg aggctctggc     780
ggtggtggca gtggtggcgg agggtcagga ggtggtggaa gcatcacctg ccctccacct     840
atgtccgtgg aacacgcaga catctgggtc aagagctaca gcttgtactc ccgcgagcgc     900
tacatttgta actctggttt caagcgtaaa gccggcacct gcagcctgac cgagtgcgtg     960
ttgaacaagg ccaccaatgt cgcccactgg acaaccccaa gtctcaaatg cattcgcgac    1020
cctgccctgg ttcaccaacg cccagcgcca ccatccacag taaccactgc aggcgtgacc    1080
ccacagccag agagcctctc cccttctggc aaagagccag cagcttcatc tccaagctca    1140
aacaacacag cggccacaac agcagctatt gtccgggct cccagctgat gccttcaaaa    1200
tcaccttcca caggcaccac agagatcagc agtcatgagt cctcccacgg cacccccatct    1260
cagacaacag ccaagaactg ggaactcaca gcatccgcct ccaccagcc gccaggtgtg    1320
tatccacagg gccacagcga caccacttga                                       1350
```

<210> SEQ ID NO 18
<211> LENGTH: 1015
<212> TYPE: DNA
<213> ORGANISM: ARTIFICIAL
<220> FEATURE:
<223> OTHER INFORMATION: IL-15R alpha-shushi+(73)(S40C)-Fc vector
      sequence

<400> SEQUENCE: 18

```
atggacatgc gggtgccagc ccagctgctg ggcctgttgc tgctgtggtt ccccggctct      60
cggtgcatca cctgccctcc acctatgtcc gtgaacacg cagacatctg gtcaagagc     120
tacagcttgt actcccgcga gcgctacatt tgtaactctg gtttcaagcg taaagccggc     180
acctgcagcc tgaccgagtg cgtgttgaac aaggccacca atgtcgccca ctggacaacc     240
ccaagtctca aatgcattcg cgaccctgcc ctggttcacc aacgcggcgg aggaggctct     300
gggggcggag gaagcgaacc taagtcctct gataagaccc acacatgtcc ccctgccca     360
gctcctgagc tcttgggcgg accttccgtg tttctgttcc ccccaaagcc caaggatacc     420
```

-continued

```
cttatgatca gcagaacacc cgaagttact tgcgtggtcg tggacgtttc tcacgaagat      480
cctgaagtga aattcaactg gtacgtggat ggcgtggagg tgcacaatgc taagactaag      540
ccccgtgaag agcagtacaa ctctacctac cgggtcgttt cagtgctgac tgttctccat      600
caggactggc tcaacgggaa ggagtataag tgcaaggtgt ctaacaaggc actgcccgca      660
cccatcgaga agaccatttc taaggccaag ggtcaaccac gggagccaca ggtttacaca      720
ttgcctccca gtcgggagga tgacaaag aatcaagtgt cacttacatg tcttgtgaag        780
ggcttctacc cctcagacat cgccgtggag tgggagagca acggacaacc agaaaacaac      840
tacaagacca cacctcctgt gctcgattca gatggttcct tttcttgta cagcaaactc       900 accgttgaca agagtcggtg gcagcaagga aatgtgttca gctgttctgt gatgcacgag      960
gccctgcaca accattatac ccaaaaatct ctcagccttt ctcccggcaa gtgac          1015
```

<210> SEQ ID NO 19
<211> LENGTH: 1044
<212> TYPE: DNA
<213> ORGANISM: ARTIFICIAL
<220> FEATURE:
<223> OTHER INFORMATION: Fc-IL-15R alpha -shushi+(73)(S40C)vector
      sequence

<400> SEQUENCE: 19

```
atggacatgc gggtgccagc ccagctgctg ggcctgttgc tgctgtggtt ccccggctct      60
cggtgcgaac ctaagtcctc tgataagacc cacacatgtc cccctgccc agctcctgag       120 ctcttgggcg gaccttccgt gtttctgttc cccccaaagc ccaaggatac ccttatgatc      180
agcagaacac ccgaagttac ttgcgtggtc gtggacgttt ctcacgaaga tcctgaagtg      240
aaattcaact ggtacgtgga tggcgtggag gtgcacaatg ctaagactaa gccccgtgaa      300
gagcagtaca actctaccta ccgggtcgtt tcagtgctga ctgttctcca tcaggactgg      360
ctcaacggga aggagtataa gtgcaaggtg tctaacaagg cactgcccgc acccatcgag      420
aagaccattt ctaaggccaa gggtcaacca cgggagccac aggtttacac attgcctccc      480
agtcgggagg atgacaaaga atcaagtgtc acttacatgt cttgtgaag ggcttctac       540 ccctcagaca tcgccgtgga gtgggagagc aacggacaac cagaaaacaa ctacaagacc     600
acacctcctg tgctcgattc agatggttcc ttttcttgt acagcaaact caccgttgac      660
aagagtcggt ggcagcaagg aaatgtgttc agctgttctg tgatgcacga ggccctgcac     720
aaccattata cccaaaaatc tctcagcctt tctcccggca agggcggagg aggctctggc     780
ggtggtggca gtggtggcgg agggtcagga ggtggtggaa gcatcacctg ccctccacct     840
atgtccgtgg aacacgcaga catctgggtc aagagctaca gcttgtactc ccgcgagcgc     900
tacatttgta actctggttt caagcgtaaa gccggcacct gcagcctgac cgagtgcgtg     960
ttgaacaagg ccaccaatgt cgcccactgg acaaccccaa gtctcaaatg cattcgcgac     1020
cctgccctgg ttcaccaacg ctga                                           1044
```

```
<210> SEQ ID NO 20
<211> LENGTH: 696
<212> TYPE: DNA
<213> ORGANISM: ARTIFICIAL
<220> FEATURE:
<223> OTHER INFORMATION: Fc fragment,IgG1-Fc

<400> SEQUENCE: 20
gaacctaagt cctctgataa gacccacaca tgtcccccct gcccagctcc tgagctcttg      60
ggcggacctt ccgtgtttct gttcccccca agcccaagg  ataccttat  gatcagcaga     120 acacccgaag ttacttgcgt ggtcgtggac gtttctcacg aagatcctga agtgaaattc     180
aactggtacg tggatggcgt ggaggtgcac aatgctaaga ctaagcccccg tgaagagcag    240 tacaactcta cctaccgggt cgtttcagtg ctgactgttc tccatcagga ctggctcaac    300
gggaaggagt ataagtgcaa ggtgtctaac aaggcactgc ccgcacccat cgagaagacc    360
atttctaagg ccaagggtca accacggag ccacaggttt acacattgcc tcccagtcgg     420
gaggagatga caaagaatca agtgtcactt acatgtcttg tgaagggctt ctaccctca    480 gacatcgccg tggagtggga gagcaacgga caaccagaaa acaactacaa gaccacacct    540
cctgtgctcg attcagatgg ttccttttc ttgtacagca aactcaccgt tgacaagagt    600
cggtggcagc aaggaaatgt gttcagctgt tctgtgatgc acgaggccct gcacaaccat    660
tatacccaaa aatctctcag cctttctccc ggcaag                             696
```

INTERLEUKIN 15 PROTEIN COMPLEX

CROSS-REFERENCE TO RELATED APPLICATION

This application is a Section 371 of International Application No. PCT/CN2015/094780, filed Nov. 17, 2015, which was published in the Chinese language on Jun. 23, 2016 under International Publication No. WO 2016/095642 A9, and the disclosure of which is incorporated herein by reference

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688452_47US", creation date of Jun. 15, 2017, and having a size of 35.1 KB. The sequence listing submitted via EFS-Web is part of the specification and is herein incorporated by reference in its entirety.

FIELD OF THE INVENTION

The present invention relates to an IL-15 protein complex and uses thereof, and further relates to a soluble IL-15/IL-15Rα protein complex, and its use as a therapeutic agent, particularly as a therapeutic agent for cancer and autoimmune disease.

BACKGROUND OF THE INVENTION

Interleukin 15 (IL-15), discovered by Grabstein et al. in 1994, is a cytokine about 12-14 kD, which plays a role in the normal immune response of organisms, such as promoting the proliferation of T cells, B cells and natural killer (NK) cells.

IL-15 is a member of the small four α-helix bundle family of cytokines. IL-15 needs to bind with its receptor to exert biological activity. The IL-15 receptor consists of three receptor subunits: IL-15 receptor α (IL-15Rα), IL-2 receptor β (IL-2Rβ, also known as IL-15Rβ or CD122) and γc (also known as CD132). IL-15Rα contains a Sushi domain, which is capable of binding with IL-15, and is essential for biological functions of IL-15 after binding.

Recently, it was discovered that the complex formed by IL-15 and its receptor IL-15Rα can significantly enhance the biological activity of IL-15. Studies indicated that the complex formed by IL-15 and soluble IL-15Rα receptor is significantly superior to IL-15 alone in stimulating the proliferation of memory CD8+ T lymphocytes and NT/NKT cells. The IL-15/IL-15Rα significantly expanded and induced the proliferation of CD122 high cells, including the memory CD8+ T lymphocytes, which have been stimulated by antigens. The IL-15/IL-15Rα complex is more than 10 fold stronger than IL-15 alone in stimulating proliferation of memory CD8+ T cells and in maintaining their survival; the mechanism may be related to trans-presentation.

Since IL-15 has been one of the most promising candidates in the field of tumor immunotherapy, the NIH first began investigating IL-15 treatment for tumors, and tried to push it into Phase I clinical trials. However, IL-15 has the disadvantages of a small molecular weight, short in vivo half-life, poor repeatability of dosage, and is likely to cause systemic immune side effects. There is an urgent need to find an approach that can increase the in vivo half-life, and promote or enhance the biological activity of IL-15 in vivo. There are many domestic and foreign companies and research institutions engaging in research related to IL-15 immunotherapy. See for example, Chinese Patent CN100334112C (Shanghai Haixin Biotechnology Co., Ltd.) related to IL-15-hIgG4Fc homodimeric protein for antimicrobial infection treatment. Introducing a disulfide bond between IL-15 and IL-15Rα complex molecules of the present invention can increase the molecular stability and bioactivity as while as simplify the manufacturing process.

SUMMARY OF THE INVENTION

The present invention provides a protein molecule with prolonged in vivo half-life, increased in vitro activity and significant anti-tumor activity designed and prepared via genetic engineering methods.

The present invention provides an IL-15 protein complex comprising a soluble fusion protein (I) and a soluble fusion protein (II), wherein:
the soluble fusion protein (I) is an IL-15 polypeptide or a functional fragment thereof; and the soluble fusion protein (II) is an IL-15Rα polypeptide or a functional fragment thereof;
wherein the soluble fusion protein (I) and/or the soluble fusion protein (II) possesses Cys resulting from one or more amino acid mutations, thus forming a disulfide bond by the pairing of the corresponding Cys present in the soluble fusion protein (II) and the soluble fusion protein (I).

In a preferred embodiment, the present invention provides an IL-15 protein complex, wherein said soluble fusion protein (I) and/or soluble fusion protein (II) is covalently linked to an Fc fragment or a mutant thereof.

In another preferred embodiment, the present invention provides an IL-15 protein complex, wherein the soluble fusion protein (II) is covalently linked to an Fc fragment or a mutant thereof.

In another preferred embodiment, the present invention provides an IL-15 protein complex, wherein the amino acid Cys mutation occurs on the IL-15 polypeptide or a functional fragment thereof.

In another preferred embodiment, the present invention provides an IL-15 protein complex, wherein the amino acid Cys mutation site occurs at L45, Q48, V49, L52, E53, C88 or E89 on the IL-15 polypeptide or a functional fragment thereof, preferably at L52, E53 or E89, and more preferably at L52.

In another preferred embodiment, the present invention provides an IL-15 protein complex, wherein the sequence of the soluble fusion protein (I) is SEQ ID NO: 2.

In another preferred embodiment, the present invention provides an IL-15 protein complex, wherein the amino acid Cys mutation site occurs on the IL-15Rα polypeptide or a functional fragment thereof.

In another preferred embodiment, the invention provides an IL-15 protein complex, wherein the amino acid Cys mutation site occurs at K34, L42, A37, G38 or S40 of the IL-15Rα polypeptide or a functional fragment thereof, preferably occurs at A37, G38 or S40, and more preferably at S40.

In another preferred embodiment, the present invention provides an IL-15 protein complex, wherein the soluble fusion protein (II) is constituted by recombination of an IL-15Rα polypeptide or a functional fragment thereof and an Fc fragment; preferably the IL-15Rα polypeptide or a functional fragment thereof is attached to the N-terminus of the Fc fragment; and more preferably, the Fc fragment is shown in SEQ ID NO: 9.

In another preferred embodiment, the invention provides an IL-15 protein complex, wherein the sequence of the soluble fusion protein (II) is selected from the group consisting of SEQ ID NO: 5, SEQ ID NO: 6, SEQ ID NO: 7 and SEQ ID NO: 8, preferably SEQ ID NO: 5 or SEQ ID NO: 6.

In another preferred embodiment of the present invention, an IL-15 protein complex is selected from the following combinations of a soluble fusion protein (I) and a soluble fusion protein (II):

| NO. | soluble fusion protein (I) | soluble fusion protein (II) |
| --- | --- | --- |
| 1 | IL-15 (L52C) (SEQ ID NO: 2) | IL-15Rα-ECD(S40C)-Fc (SEQ ID NO: 5) |
| 2 | IL-15 (L52C) (SEQ ID NO: 2) | Fc-IL-15Rα-ECD (S40C) (SEQ ID NO: 6) |
| 3 | IL-15 (L52C) (SEQ ID NO: 2) | IL-15Rα-Sushi + (S40C)-Fc (SEQ ID NO: 7) |
| 4 | IL-15 (L52C) (SEQ ID NO: 2) | Fc-IL-15Rα-sushi + (S40C) (SEQ ID NO: 8) |

The present invention also relates to a nucleic acid encoding the IL-15/IL-15Rα protein complex as described above.

The present invention also relates to a DNA vector comprising a nucleic acid as described above.

The present invention also relates to a host cell comprising a DNA vector as described above.

The present invention also relates to a method for preparing a protein complex of IL-15/IL-15Rα as described above, the method comprises: culturing the host cell of the present invention under a condition sufficient for the expression of the IL-15/IL-15Rα protein complex as described above; and expressing and purifying the IL-15/IL1-5Rα protein complex.

The present invention also relates to a pharmaceutical composition comprising the IL-15/IL1-5Rα protein complex of the present invention, and a pharmaceutically acceptable excipient, diluent or carrier The present invention also relates to a method for stimulating or inhibiting the immune response in a mammal, comprising: administering to the mammal a therapeutically effective amount of the IL-15/IL1-5Rα protein complex according to the present invention, or the pharmaceutical composition according to the present invention.

The present invention also relates to use of the IL-15/IL1-5Rα protein complex according to the present invention, or the pharmaceutical composition according to the present invention, in the preparation of a medicament for the treatment of IL-15-mediated diseases or disorders; wherein the disease is selected from the group consisting of infectious diseases, cancer, blood disease and autoimmune disease. The cancer is selected from the group consisting of melanoma, colorectal cancer, skin cancer, lymphoma, renal cell carcinoma, solid tumor, liver cancer, lung cancer, stomach cancer, and breast cancer; the infectious disease is selected from the group consisting of variola virus infection, HIV infection, bacterial infection, fungal infection, and HBV infection; the blood disease is selected from the group consisting of anemia, acute myeloid leukemia, myelodysplastic syndrome, and T-cell large granular lymphocytic leukemia; the autoimmune disease is selected from the group consisting of multiple sclerosis disease, psoriasis, rheumatoid arthritis, inflammatory diseases, gastritis and mucosal inflammation. The IL-15/IL-15Rα protein complex or the pharmaceutical composition can be used alone or in combination with other drugs. The other drug is a small molecule inhibitor or an antibody drug; The small molecule inhibitor(s) is/are preferably selected from targeted chemotherapeutic or radiotherapeutic agents, more preferably alkylating agent(s); the antibody drug(s) is/are preferably selected from monoclonal antibody(ies), more preferably anti-CD20, anti-PD1, anti-PDL1, anti-Her2, anti-EGFR, or anti-c-MET antibody(ies).

The present invention also relates to a method for treating or preventing a disease, which includes but is not limited to chemotherapy, radiotherapy, surgical treatment, etc. Disease-associated antigen is expressed in the disease. The method comprises administering to a patient an IL-15/IL-15Rα protein complex as described above or a pharmaceutical composition as described above; forming a specific binding complex between the cells expressing the disease-associated antigen and the immune cells expressing IL-15Rα, sufficient for activating those immune cells; and killing those cells expressing disease-associated antigen via the immune cells. The cells expressing disease-associated antigen are preferably tumor cells or virus-infected cells. The immune cells are preferably T-cells, LAK cells or NK cells. The disease is selected from the group consisting of infectious disease, cancer, blood disease and autoimmune disease. The cancer is preferably selected from the group consisting of melanoma, colorectal cancer, skin cancer, lymphoma, renal cell carcinoma, solid tumor, liver cancer, lung cancer, stomach cancer, and breast cancer. The infectious disease is selected from the group consisting of variola virus infection, HIV infection, bacterial infection, fungal infection and HBV infection. The blood disease is selected from the group consisting of anemia, acute myeloid leukemia, myelodysplastic syndrome, and T-cell large granular lymphocytic leukemia. The autoimmune disease is selected from the group consisting of multiple sclerosis, psoriasis, rheumatoid arthritis, inflammation disease, gastritis, and mucosal inflammation.

The present invention also relates to a method of combination therapy for treating or preventing a disease, comprising administering to a patient an IL-15/IL-15Rα protein complex as described above or a pharmaceutical composition as previously described, in combination with other drugs, such as a small molecule inhibitor or an antibody drug. The small molecule inhibitor(s) is/are preferably selected from targeted chemotherapeutic or radiotherapeutic agents, more preferably alkylating agent(s); the antibody drug(s) is/are preferably selected from monoclonal antibody(ies), more preferably anti-CD20, anti-PD1, anti-PDL1, anti-Her2, anti-EGFR, and anti-c-MET antibody(ies).

For better understanding of the present disclosure, certain technical and scientific terms are specifically defined below. Unless specifically defined elsewhere in this document, all other technical and scientific terms used herein have the meaning commonly understood by one of ordinary skill in the field to which this disclosure belongs.

Terms

As used herein, the single-letter code and the three-letter code for amino acids are as described in *J. Biol. Chem,* 243, (1968) p 3558.

In the present invention, the "protein complex" or "complex protein" of the present invention refers to a protein formed by binding of two different monomeric proteins.

In the present invention, the monomeric protein (i.e., soluble fusion protein (I), soluble fusion protein (II)) from which the protein complex is formed can be a fusion protein or a non-fusion protein.

As used herein, "fusion protein" refers to a protein product obtained by linking the coding regions of two or more genes by using recombinant genetic methods, chemical methods or other suitable methods; and expressing the recombinant gene under control of an identical regulatory sequence. In some embodiments of the present invention, the soluble fusion protein (I) is a monomeric protein obtained by fusion or non-fusion expression of IL-15 or a variant thereof with a biologically active polypeptide such as an Fc fragment; and the soluble fusion protein (n) is a monomeric protein obtained by fusion or non-fusion expression of IL-15Rα or a variant thereof with a biologically active polypeptide such as an Fc fragment. In the fusion proteins of the invention, the coding regions of two or more genes can be fused by sequence(s) encoding peptide linker(s) in one or several location(s). Peptide linkers can also be used to construct the fusion protein of the invention.

As used herein, "IL-15" or "functional fragment" can be any IL-15 (interleukin-15) or a mutant thereof, such as human or non-human mammalian IL-15 or non-mammalian IL-15. Exemplary non-human mammals include, such as, pigs, rabbits, monkeys, chimpanzees, mice, and the like; non-mammals include, such as, chickens and the like. Preferably, IL-15 and functional fragments thereof are human. Human interleukin-15 mature molecule (SEQ ID NO: 1) is found in the Database UniProtKB, under Accession Number P40933, 49-162aa. The term "IL-15 functional fragment" refers to a mutant obtained by one or more amino acid substitutions, additions or deletions, with altered effects on IL-15 biological function or other properties. Such amino acid alterations can increase or decrease the interaction between IL-15 and its receptor IL-15Rα or IL-15Rβ; or increase or decrease the biological activity of IL-15, such as its activity in stimulating proliferation of immune cells; or such amino acid mutations can establish covalent bonds between IL-15 and its receptor, or make the covalent linkage more stable. For example, IL-15 (L52C), i.e., at position 52, the leucine L is replaced with cysteine C (SEQ ID NO: 2), and certain amino acids on IL-15Rα corresponding to this site are substituted with C to form a disulfide bond with it.

As used herein, "IL-15Rα" or "functional fragment" can be any IL-15Rα or a functional fragment thereof from any species, such as human or non-human mammalian IL-15Rα or non-mammalian IL-15Rα. Exemplary non-human mammals include, such as, pigs, rabbits, monkeys, chimpanzees, mice, and the like; non-mammals include, such as, chickens and the like. Preferably, IL-15Rα is human, and more preferably is an extracellular domain portion of human interleukin-15 receptor α, referred to as IL-15Rα ECD (SEQ ID NO: 3), see Database UniProtKB, under Accession Number Q13261, 31-205aa. The term "IL-15Rα functional fragment" preferably is a shortened form of the extracellular domain fragment of IL-15Rα, that is, a molecule comprising a sushi domain obtained by one or more amino acid substitutions, insertions or deletions, with human interleukin 15 receptor α activity, such as IL-15Rα-sushi+(SEQ ID NO: 4).

The term "Fc fragment" refers to a human immunoglobulin chain constant region, especially the C-terminus or a part of the immunoglobulin heavy chain constant region, having no antigen-binding activity, and is a site for the interaction between an antibody molecule and an effector molecule or cells. For example, an immunoglobulin Fc region can comprise two or more domains of the heavy chain CH1, CH2, CH3 and CH4, in combination with an immunoglobulin hinge region. According to the amino acid sequence of the heavy chain constant region, immunoglobulins can be divided into different categories, mainly into five classes of immunoglobulins: IgA, IgD, IgE, IgG and IgM. Some of them can be further divided into subtypes (isotypes), e.g. IgG-1, IgG-2, IgG-3, IgG-4; IgA-1, IgA-2 and different genotypes.

An "Fc fragment" preferably comprises at least one immunoglobulin hinge region, and CH2 and CH3 regions of IgG, and more preferably comprises a CH2 domain, a CH3 domain and an immunoglobulin hinge region, wherein the initial amino acid position of hinge region can be varied.

The term "linker peptide (Linker)" in the present invention is a peptide used to connect IL-15 or IL-15Rα with an Fc variant, in order to ensure the correct protein folding and stability. A "linker peptide" of the present invention is preferably (GGGGS) n, wherein n can be 0, 1, 2, 3, 4, 5 or more, preferably n is 2-4. If the sequence of the linker peptide is too short, the advanced structure folding of two proteins can be affected, and thus interfere with each other; if the sequence of the linker peptide is too long, the problem of immunogenicity is a concern, since the linker peptide sequence itself is a new antigen.

As used herein, "protein complex" is preferably a product of the co-expressed genes, for example, co-expressed in prokaryotic cells such as *E. coli*; or co-expressed in eukaryotic cells, such as 293 and CHO.

As used herein, "coexpression" refers to the expression of multiple genes together in a cell to simultaneously generate their products. These genes can be simultaneously existing and separately or commonly controlled and expressed. In the present invention, two genes are preferably co-expressed in a eukaryotic cell. A product obtained by co-expression of genes is conducive to form a complex efficiently and easily.

"Administration" or "treatment," as it applies to biological materials, such as an animal, human, experimental subject, cell, tissue, organ, or biological fluid, refers to contact of an exogenous pharmaceutical, therapeutic agent, diagnostic agent, or composition with the biological material including animal, human, subject, cell, tissue, organ, or biological fluid. "Administration" or "treatment" can refer, e.g., to therapeutic, pharmacokinetic, diagnostic, research, and experimental methods. Treatment of a cell encompasses contacting a reagent with the cell, as well as contacting a reagent with a fluid, wherein the fluid is in contact with the cell. "Administration" or "treatment" also means in vitro and ex vivo treatments, e.g., of a cell, with a reagent, diagnostic, binding compound, or with another cell. "Treatment," as it applies to a human, animal, or a subject, refers to therapeutic treatment, prophylactic or preventative measures, and to research and diagnostic applications. "Treatment", as it applies to a human, animal, or a subject, or cell, tissue, or organ, encompasses contacting an IL15 agonist or IL15 antagonist with a human or animal, a subject, a cell, tissue, physiological compartment, or physiological fluid. "Treatment of a cell" encompasses the situation where the IL15 agonist or IL15 antagonist contacts with IL15 receptor, e.g., in the fluid phase or colloidal phase, and also encompasses the situation where the agonist or antagonist does not contact the cell or the receptor.

"Treat" means to administer internally or externally a therapeutic agent, such as an IL-5 protein complex of the present invention or a composition containing the same, to a patient suffering from one or more diseases or conditions selected from "immune" or "cancer". The therapeutic agent is known to have therapeutic effects on these diseases or conditions. Typically, the therapeutic agent is administered in an amount effective to alleviate one or more diseases or conditions in the patient or population to be treated, either by inducing the regression of these diseases or conditions or by inhibiting the progression of such diseases or conditions to any clinically measurable degree. The amount of a therapeutic agent that is effective to alleviate any particular disease or condition (also referred to as the "therapeutically effective amount") can vary according to several factors, such as the disease status, age, and body weight of the patient, and the ability of the drug to elicit a desired response in the patient.

An "immune disease" or "immune disorder" includes e.g., pathological inflammation, inflammatory disorder, and autoimmune disease or disorder. "Immune disease" also refers to infection, persistent infection, and proliferative disorders such as cancer, tumor, and angiogenesis. "Cancerous disease" includes, e.g., cancer, cancer cells, tumor, angiogenesis, and precancerous lesion, e.g., dysplasia.

As used herein, "polymerase chain reaction" or "PCR" refers to an amplification procedure or technique described in, e.g., U.S. Pat. No. 4,683,195. Generally, sequence information from the ends of the region of interest or beyond the region of interest needs to be available, such that oligonucleotide primers can be designed. These primers will be identical or similar in sequence to the strand opposite to the template to be amplified.

"Optional" or "optionally" means that the event or situation that follows may but does not necessarily occur, and the description includes the instances in which the event or circumstance does or does not occur. For example, "optionally contains 1-3 antibody heavy chain variable regions" means the antibody heavy chain variable region can be, but not necessarily needs to be, present, and if present can be 1, 2 or 3.

"Pharmaceutical composition" refers to a mixture containing one or more compounds according to the present invention or a physiologically/pharmaceutically acceptable salt or prodrug thereof with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

Transformation of the host cell with the recombinant DNA can be carried out by conventional techniques well known to those skilled in the art. The obtained transformants are cultured by using conventional methods to express the polypeptide encoded by the gene of the invention. Culture medium can be selected from various conventional culture mediums based on the host cells used. The host cells grow under proper conditions.

DETAILED DESCRIPTION OF THE INVENTION

Hereinafter, the present invention is further described with reference to examples. However, the scope of the present invention is not limited thereto.

In the examples of the present invention, where specific conditions are not described, the experiments are generally conducted under conventional conditions, or under conditions proposed by the material or product manufacturers. See Sambrook et al., Molecular Cloning, A Laboratory Manual, Cold Spring Harbor Laboratory; Current Protocols in Molecular Biology, Ausubel et al, Greene Publishing Associates, Wiley Interscience, NY. Where the source of the reagents is not specifically given, the reagents are commercially available conventional reagents.

Example 1. Selection and Verification of the Mutants

IL-15 is a promising cytokine for the treatment of cancer and viral diseases. It can be presented to IL-15 receptor β/γ located on the surface of T cells and NK cells by IL-15Rα (IL-15 receptor α), thereby stimulating the proliferation of the activated T cells. Therefore, increasing the binding capacity of IL-15 and IL-15 receptor α will significantly enhance the functions of a variety of lymphocytes, which is very important for immunotherapy.

Figure 1:
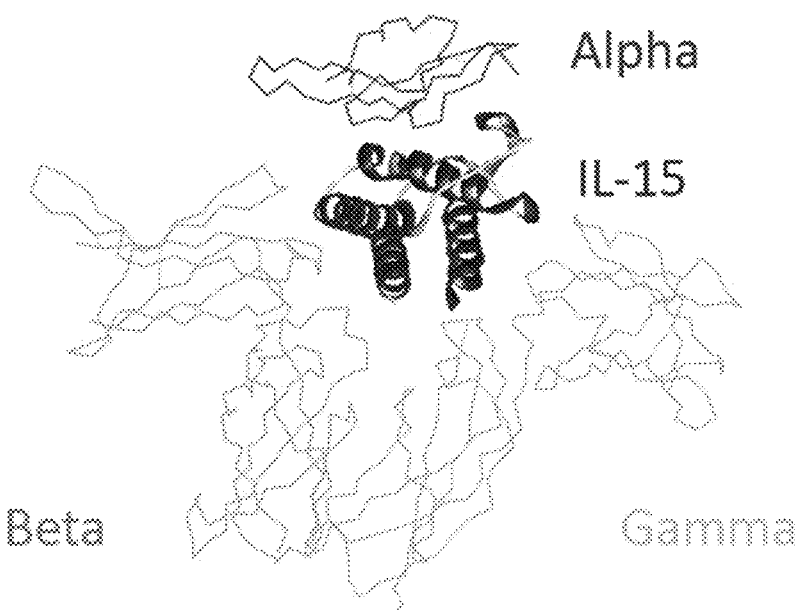
FIG. 1 shows a crystal complex structure of IL-15 and the receptor α, β, γ.
Figure 2:
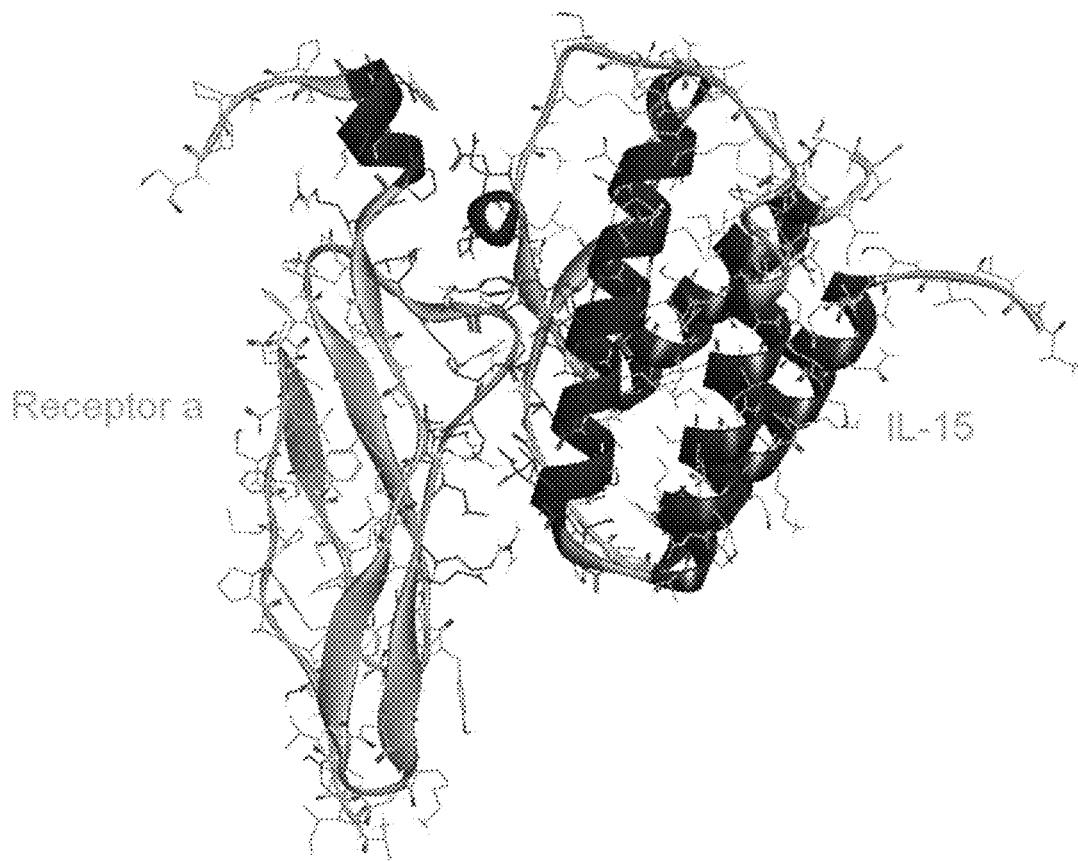
FIG. 2 shows residues at the interface of IL-15 and IL-15Rα (receptor α).

It can be seen that the three receptors bind to IL-15 in three different orientations, respectively, from the crystalline complex structure of IL-15 and the receptor α, β, γ (PDB ID: 4GS7) (FIG. 1). Therefore, when the residues present on the interface between IL-15 and receptor α are modified, the binding of IL-15 to receptors β and γ will not be affected.

Figure 3:
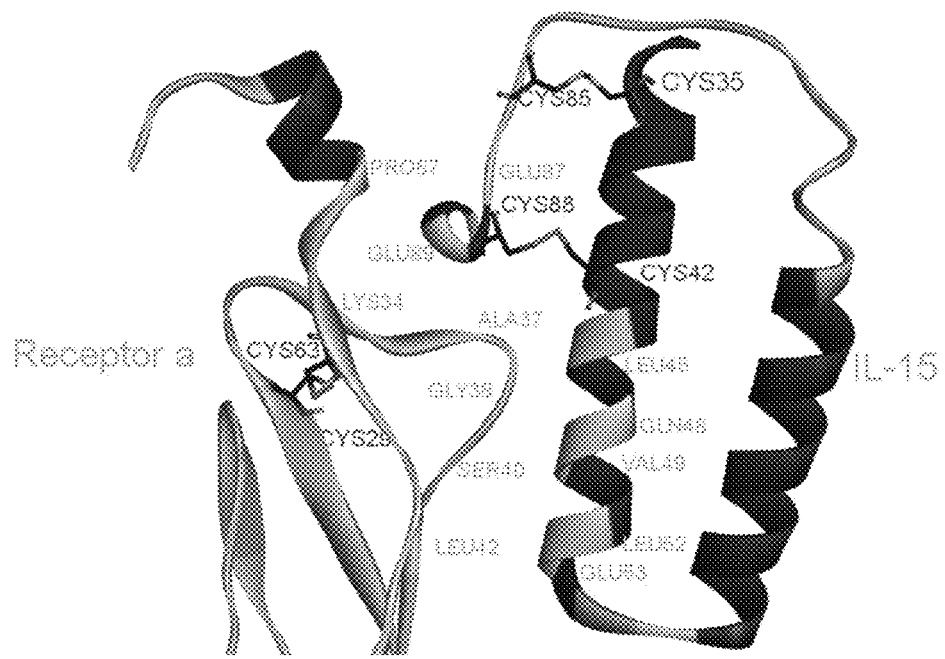
FIG. 3 shows relative positions of candidate mutant residues located on IL-15 and IL-15Rα.

The present inventors selected the co-crystal structure (PDB ID: 2Z3Q) of IL-15 and receptor α as the initial structure (the crystal structure of Receptor α in this structure is slightly longer than that in 4GS7). The residues located on the interface of IL-15 and receptor α are summarized from the structure (Table 1). The cut-off value was set at 6 Å from the opposite molecule (FIG. 2).

TABLE 1

Residues at the contacting interface of IL-15 and receptor α crystal complex

| Molecule | Residues at the contacting interface |
|---|---|
| IL-15 | H20, I21, D22, A23, T24, L25, Y26, C42, L45, E46, Q48, V49, L52, E53, S54, G55, E87, C88, E89, E90, E93, K94 |
| receptor α | R24, R26, K34, R35, K36, A37, G38, T39, S40, S41, L42, E44, S60, I64, R65, D66, P67, A68, V70, H71, Q72 |

Disulfide scanning was performed at the interface between IL-15 and receptor α by using Disulfide Scan in the Simulation software MOE. The basic principle of scanning is to look for a combination of residues located at IL-15 and IL-15 receptor α, respectively, within the disulfide bond length range, so as to obtain the following combination of residues (Table 2) and the relative positions of candidate mutant residues (FIG. 3).

TABLE 2

Combination of the Mutated Residues at IL-15 and IL-15 Receptor α

| IL-15 | Receptor α | D stability (Kcal/mol) |
|---|---|---|
| L45C | A37C | −4.1933 |
| L45C | G38C | −3.4475 |
| Q48C | G38C | −5.7596 |
| V49C | S40C | −3.6957 |
| L52C | S40C | −4.0172 |
| E53C | L42C | −3.3652 |
| E87C | P67C | −2.8417 |
| C88C | A37C | −4.0382 |
| E89C | K34C | −7.3065 |

Selection for the mutation combination was performed according to the following principles. (1) Do not select the residues near the intramolecular disulfide bond, so as to avoid matching error, and then avoid mispairing of the original intramolecular disulfide bond. (2) Try to choose the residues which will not affect the three-dimensional structure of the protein following mutation. (3) Select the residues which will minimize the effect the energy on the whole structure following mutation.

In order to meet the above requirement 1, from the crystal structure of complex, it can be seen that on the structure of IL-15, intramolecular disulfide bonds were formed between C35 and C85, and between C42 and C88, respectively. Therefore, it is possible to exclude the possibility of E87 and E89, upstream and downstream of C88, respectively, as the candidate residues on IL-15, and exclude the possibility of P67 and K34 on the corresponding receptor α as the candidate residues. In addition, it is necessary to exclude the possibility of a disulfide bond formed by the C88 residue at IL-15 with the A37 residue at the receptor α. On the structure of receptor α, C29 and C63 form a disulfide bond. No candidate residues were found near the pair.

In order to meet the above requirement 2, the crystallization complex was analyzed. First, L45, Q48, V49, L52 and E53 were all located at the alpha helix on the IL-15 structure. In addition, L45, Q48 and V49 were all located in the middle of the alpha helix. If these residues are mutated to Cys, the torsion of the side chain caused by the formation of the disulfide bond may have an influence on the structure of the original alpha-helix, and then affect the whole protein structure. Therefore, L52 and E53 residues on the IL-15 were considered as preferred. Second, on the structure of IL-15 receptor alpha, L42 was located at the beta fold, A37, G38 and S40 were all located at the loop. Therefore, A37, G38 and S40 present on IL-15 receptor alpha were considered as preferred. In view of the two structures, L52 from IL-15 and S40 from the IL-15 receptor alpha were considered as preferred for mutation to Cys, and finally which led to the formation of a intermolecular disulfide bond.

Figure 4:
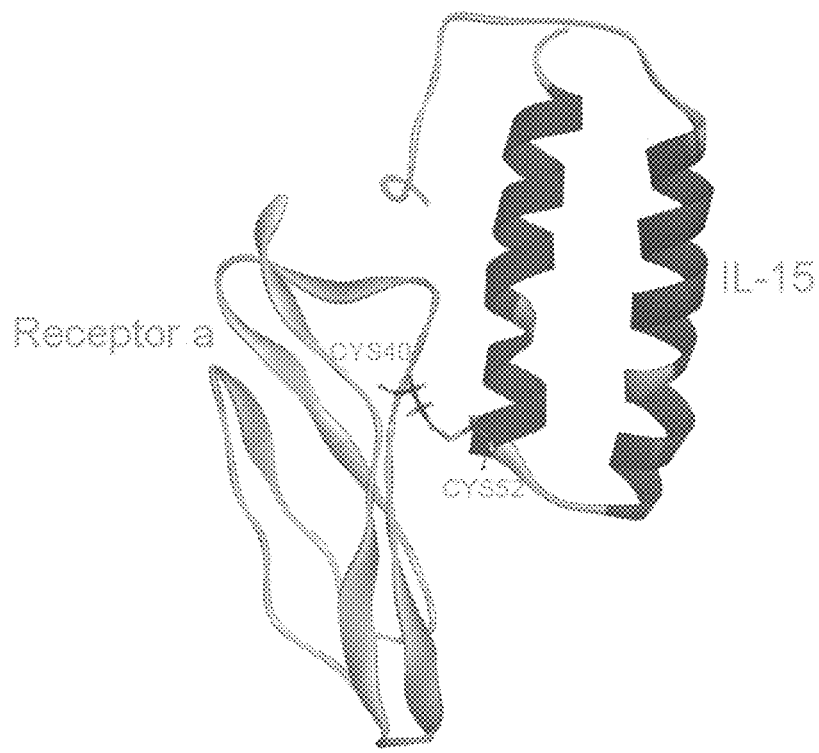
FIG. 4 is a model diagram of a disulfide bond formed between L52C on IL-15 and S40C on IL-15Rα.

In order to meet the above requirement 3, alanine scanning was performed on all of the above residues by using Discovery Studio Computational Software. The results of energy change calculated in the mutations (Table 3) show that L52A present on IL-15 minimally affected the structural stability, and S40A present on IL-15 receptor α minimally affected the structural stability. Therefore, from the above results, L52 from IL-15 and S40 from the IL-15 receptor alpha can be considered as preferred candidates for mutation to Cys, and finally for the formation of the intermolecular disulfide bond (FIG. 4).

TABLE 3

Alanine scanning results

| Molecule | Mutants | Mutation Energy (Kcal/mol) |
|---|---|---|
| IL-15 | LEU52 > ALA | 0.65 |
| IL-15 | GLU89 > ALA | 1.66 |
| IL-15 | GLN48 > ALA | 1.67 |
| IL-15 | LEU45 > ALA | 1.69 |
| IL-15 | GLU53 > ALA | 2.12 |
| IL-15 | VAL49 > ALA | 2.86 |
| IL-15 Receptor α | SER40 > ALA | −0.81 |
| IL-15 Receptor α | ALA37 > ALA | 0 |
| IL-15 Receptor α | GLY38 > ALA | 1.31 |
| IL-15 Receptor α | LEU42 > ALA | 2.65 |
| IL-15 Receptor α | LYS34 > ALA | 2.98 |

In summary, a total of 8 pairs of mutation residues were designed. Among these, L52 from IL-15 and S40 from the IL-15 receptor alpha are considered as preferred for mutation to Cys, and finally for the formation of the disulfide bond.

Based on the above 8 pairs of the mutation residues, the molecules were designed for cell expression verification. There are two forms. One is IL-15-Fc fusion molecule with Cys mutation co-expressed with IL-15Rα with Cys mutation (combinations 10-18), and the other is IL-15-6His with Cys mutation co-expressed with IL-15Rα-Fc fusion molecule with Cys mutation (combinations 1-9). The cell supernatant obtained from the co-expression was subjected to Western blot analysis. The His labeled part of the co-expression product combinations 1-9 was detected with anti-mouse His (primary antibody, abcam, ab14923) and goat anti-mouse HRP (secondary antibody, Jackson, 115-035-062); and the Fc part of the co-expression product combinations 1-18 was detected with goat anti-human Fc-HRP (Jackson, 109-035-098). The specific co-expression combinations are shown in Table 4.

TABLE 4

Co-expression combinations of different mutations

| Co-expression combination NO. | Clone |
|---|---|
| 1 | IL-15-His<br>IL-15Rα-linker-Fc |
| 2 | IL-15(L45C)-His<br>IL-15Rα(A37C)-linker-Fc |
| 3 | IL-15(L45C)-His<br>IL-15Rα(G38C)-linker-Fc |
| 4 | IL-15(Q48C)-His<br>IL-15Rα(G38C)-linker-Fc |
| 5 | IL-15(V49C)-His<br>IL-15Rα(S40C)-linker-Fc |
| 6 | IL-15(L52C)-His<br>IL-15Rα(S40C)-linker-Fc |
| 7 | IL-15(E53C)-His<br>IL-15Rα(L42C)-linker-Fc |
| 8 | IL-15(C88)-His<br>IL-15Rα(A37C)-linker-Fc |
| 9 | IL-15(E89C)-His<br>IL-15Rα(K34C)-linker-Fc |

TABLE 4-continued

Co-expression combinations of different mutations

| Co-expression combination NO. | Clone |
|---|---|
| 10 | IL-15-linker-Fc |
| | IL-15Rα |
| 11 | IL-15(L45C)-linker-Fc |
| | IL-15Rα(A37C) |
| 12 | IL-15(L45C)-linker-Fc |
| | IL-15Rα(G38C) |
| 13 | IL-15(Q48C)-linker-Fc |
| | IL-15Rα(G38C) |
| 14 | IL-15(V49C)-linker-Fc |
| | IL-15Rα(S40C) |
| 15 | IL-15(L52C)-linker-Fc |
| | IL-15Rα(S40C) |
| 16 | IL-15(E53C)-linker-Fc |
| | IL-15Rα(L42C) |
| 17 | IL-15(C88)-linker-Fc |
| | IL-15Rα(A37C) |
| 18 | IL-15(E89C)-linker-Fc |
| | IL-15Rα(K34C) |

Figure 5:
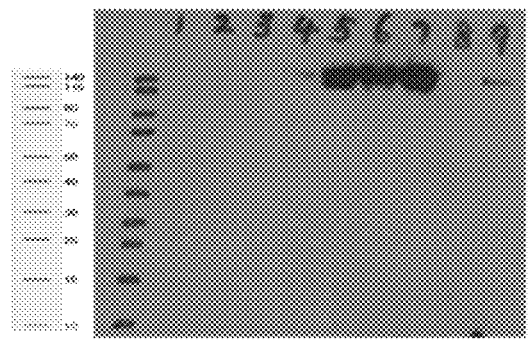
FIG. 5 shows Western blot analysis for detection of a His tag on the co-expressed molecule products 1-9 of the present invention.
Figure 6:
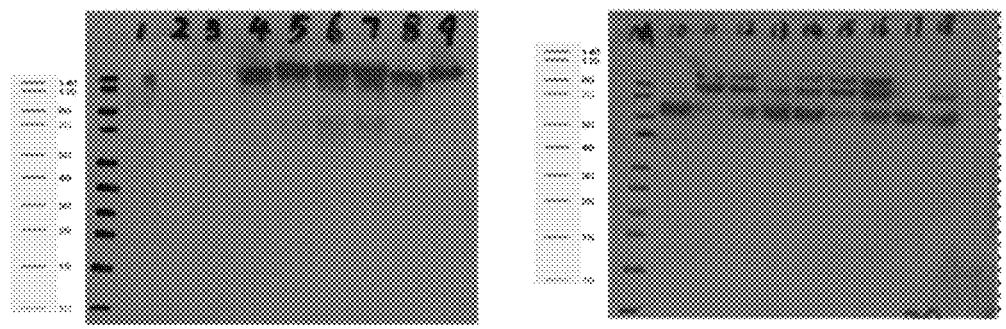
FIG. 6 shows Western blot analysis for detection of the Fc portion on co-expressed molecule products 1-18 of the present invention.

Western blot analysis showed that co-expression by pairing Fc-fused IL-15 and IL-15Rα was prone to result in mismatch, and to reduce the amount of correctly paired target product. However, following fusion with Fc, pairing Fc-fused IL-15Rα and IL-15 can result in a correctly pairing single molecule. Among them, the expression levels of co-expression combinations 5, 6 and 7 were highest, the product was highly homogeneous and the size of the bands was as expected (FIG. 5-6). The results were in good agreement with the prediction from simulation. Considering results from both computer simulation and the properties of products expressed by cells, the amino acid Cys mutation sites on IL15 were selected at L45, Q48, V49, L52, E53, C88 or E89, preferably at L52, E53 or E89, and more preferably at L52. The amino acid Cys mutation sites on IL-15Rα were selected at K34, L42, A37, G38 or S40, preferably at A37, G38 or S40, and more preferably at S40. The most preferable is the mutation L52C on IL-15 pairing with S40C on IL-15Rα. Furthermore, the stability of the IL-15 protein complex can be improved by selecting two or more pairs of disulfide bonds or introducing other non cysteine mutations between IL-15 and IL-15Rα.

Example 2. Construction of Related Vectors

Materials:
Eukaryotic expression vector pcDNA3.1 (+) (Life technologies, Cat. No. V790-20); IL-15 (DNA sequence 1), IL-15Rα ECD, IL15Rα-sushi+(73) and IgG1Fc DNA fragment were synthesized by a gene synthesis company (GENEWIZ, Inc., Suzhou);
Primers were synthesized by a gene synthesis company (GENEWIZ, Inc., Suzhou).
Procedure:
1. Fragment Ligation
IL-15Rα-ECD-Fc fragment: Overlap PCR was used to form IL-15Rα-ECD-Fc fragment by joining three DNA fragments in the order of IL-15Rα-ECD, linker peptide and Fc (DNA sequence 2).
Fc-IL-15Rα-ECD fragment: Overlap PCR was used to form Fc-IL-15Rα ECD fragment by joining three DNA fragments in the order of Fc, linker peptide and IL-15Rα-ECD (DNA sequence 3).

IL-15Rα-sushi+-Fc fragment: Overlap PCR was used to form IL-15Rα-sushi+-Fc fragment by joining three DNA fragments in the order of IL-15Rα-sushi+, linker peptide and Fc (DNA sequence 4).
Fc-IL-15Rα-sushi+fragment: Overlap PCR was used to form an Fc-IL-15Rα-sushi+ fragment by joining three DNA fragments in the order of Fc, linker peptide and IL-15Rα sushi+ (DNA sequence 5).
Gene fragments containing a Cys mutation were obtained by point mutation, for example:
IL-15 (L52C): on position 52, L was mutated to C (DNA sequence 6)
IL15Rα-ECD (S40C)-Fc: on position 40, S was mutated to C (DNA sequence 7)
Fc-IL-15Rα ECD (S40C) fragment: (DNA sequence 8)
IL-15Rα-sushi+(S40C)-Fc fragment: (DNA sequence 9)
Fc-IL-15Rα-sushi+(S40C) fragment: (DNA sequence 10).
2. Introducing Restriction Site and Signal Peptide Sequence:
Restriction endonuclease KpnI site, Kozak sequence and the signal peptide sequence were introduced at the 5'-terminus of the gene fragment by PCR. The sequence between the KpnI site and the gene fragment is shown below: GGTACCTTGTGCCCGGGCGCCACCATGGACATGC-GGGTGCCAGCCCAGCTGCTGGG CCTGTTGCTGC-TGTGGTTCCCCGGCTCTCGGTGC (The underlined sequence is the KpnI restriction site, the italic sequence is the signal peptide); Termination codon TGA and NotI restriction enzyme site were introduced into the 3'-terminus of the three fragments, respectively.
3. Construction of Expression Vectors
The above gene fragments were inserted into vector pcDNA3.1 (+) by KpnI and NotI restriction enzyme sites to construct the expression vectors, such as pcDNA3.1-IL-15, pcDNA3.1-IL-15Rα-ECD-Fc, pcDNA3.1-Fc-IL-15Rα-EC, pcDNA3.1-IL-15Rα-sushi+-Fc, pcDNA3.1-Fc-IL-15Rα-sushi+ and so on. The corresponding expression plasmids were obtained.
4. Site-Directed Mutations in Gene
KOD kit (TOYOBO Cat. KOD-201) was used for site-directed mutation, with a 25 μL system comprising 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO4 and 16 μL ddH2O. Synthesis procedure is as follows: 94° C. for 2 min, 94° C. for 30 sec, 55° C. for 30 sec, 68° C. for 11 min, for 25 amplification cycles, and PCR amplification was terminated following another 11 min at 68° C. PCR product was digested with 1 μL of DpnI (NEB Cat. R0176L) for 5 hours, and then transformed into DH5a competent cells. After that, a clone was picked up for sequencing to obtain desired plasmids pcDNA3.1-IL-15 (L52C), pcDNA3.1-IL-15Rα-ECD(S40C)-Fc, pcDNA3.1-Fc-IL-15Rα-ECD(S40C), pcDNA3.1-IL-15Rα-sushi+(S40C)-Fc, pcDNA3.1-Fc-IL-15Rα-sushi-F(S40C) and the other mutant genes. The protein complex 1 involved in the example of the present invention was obtained by expressing the expression vector containing DNA sequences 6 and 7. The protein complex 3 involved in the example of the present invention was obtained by expressing the expression vector containing DNA sequences 6 and 9. The protein complex 4 involved in the example of the present invention was obtained by expressing the expression vector containing DNA sequences 6 and 10. The protein complex 2 involved in the example of the present invention was obtained by expressing the expression vector containing DNA sequences 6 and 8.

Constructing Nucleotide Sequence of Expression Plasmid

The following sequences were used for vector construction, the single horizontal line represents a signal peptide DNA sequence, the dashed line represents a peptide linker DNA sequence, and the double horizontal line represents a mutated DNA sequence.

IL-15 (DNA sequence 1, SEQ ID NO: 10):
<u>ATGGACATGCGGGTGCCAGCCCAGCTGCTGGGCCTGTTGCTGCTGTGGTTCCCCGGC</u>

<u>TCTCGGTGC</u>AACTGGGTGAATGTAATTAGTGATTTGAAAAAAATTGAAGATCTTATT

CAATCTATGCATATTGATGCTACTTTATATACGGAAAGTGATGTTCACCCGAGTTGC

AAAGTAACAGCAATGAAGTGCTTTCTCTTGGAGTTACAAGTTATTTCA<u>CTT</u>GAGTCC

GGCGATGCAAGTATTCATGATACAGTAGAAAATCTGATCATCTTAGCAAACAACAG

TTTGTCTTCTAATGGGAATGTAACAGAATCTGGATGCAAAGAATGTGAGGAACTGG

AGGAAAAAAATATTAAAGAATTTTTGCAGAGTTTTGTACATATTGTCCAAATGTTCA

TCAACACTTCTTGA

IL-1 5Rα-ECD-Fc (DNA sequence 2, SEQ ID NO: 11):
<u>ATGGACATGCGGGTGCCAGCCCAGCTGCTGGGCCTGTTGCTGCTGTGGTTCCCCGGC</u>

<u>TCTCGGTGC</u>ATCACCTGCCCTCCACCTATGTCCGTGGAACACGCAGACATCTGGGTC

AAGAGCTACAGCTTGTACTCCCGCGAGCGCTACATTTGTAACTCTGGTTTCAAGCGT

AAAGCCGGCACCTCCAGCCTGACCGAGTGCGTGTTGAACAAGGCCACCAATGTCGC

CCACTGGACAACCCCAAGTCTCAAATGCATTCGCGACCCTGCCCTGGTTCACCAACG

CCCAGCGCCACCATCCACAGTAACCACTGCAGGCGTGACCCCACAGCCAGAGAGCC

TCTCCCCTTCTGGCAAAGAGCCAGCAGCTTCATCTCCAAGCTCAAACAACACAGCG

GCCACAACAGCAGCTATTGTCCCGGGCTCCCAGCTGATGCCTTCAAAATCACCTTCC

ACAGGCACCACAGAGATCAGCAGTCATGAGTCCTCCCACGGCACCCCATCTCAGAC

AACAGCCAAGAACTGGGAACTCACAGCATCCGCCTCCCACCAGCCGCCAGGTGTGT

ATCCACAGGGCCACAGCGACACCACT<u style="text-decoration-style: dashed;">GGCGGAGGAGGCTCTGGGGGCGGAGGAAG</u>

<u style="text-decoration-style: dashed;">C</u>GAACCTAAGTCCTCTGATAAGACCCACACATGTCCCCCTGCCCAGCTCCTGAGCT

CTTGGGCGGACCTTCCGTGTTTCTGTTCCCCCCAAAGCCCAAGGATACCCTTATGAT

CAGCAGAACACCCGAAGTTACTTGCGTGGTCGTGGACGTTTCTCACGAAGATCCTG

AAGTGAAATTCAACTGGTACGTGGATGGCGTGGAGGTGCACAATGCTAAGACTAAG

CCCCGTGAAGAGCAGTACAACTCTACCTACCGGGTCGTTTCAGTGCTGACTGTTCTC

CATCAGGACTGGCTCAACGGGAAGGAGTATAAGTGCAAGGTGTCTAACAAGGCACT

GCCCGCACCCATCGAGAAGACCATTTCTAAGGCCAAGGGTCAACCACGGGAGCCAC

AGGTTTACACATTGCCTCCCAGTCGGGAGGAGATGACAAAGAATCAAGTGTCACTT

ACATGTCTTGTGAAGGGCTTCTACCCCTCAGACATCGCCGTGGAGTGGGAGAGCAA

CGGACAACCAGAAAACAACTACAAGACCACACCTCCTGTGCTCGATTCAGATGGTT

CCTTTTTCTTGTACAGCAAACTCACCGTTGACAAGAGTCGGTGGCAGCAAGGAAAT

GTGTTCAGCTGTTCTGTGATGCACGAGGCCCTGCACAACCATTATACCCAAAAATCT

CTCAGCCTTTCTCCCGGCAAGTGA

Fc-IL-15Rα-ECD (DNA sequence 3, SEQ ID NO: 12):
<u>ATGGACATGCGGGTGCCAGCCCAGCTGCTGGGCCTGTTGCTGCTGTGGTTCCCCGGC</u>

<u>TCTCGGTGC</u>GAACCTAAGTCCTCTGATAAGACCCACACATGTCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTTCTCCATCAGGACTGGCTCAACGGGAAGGAGTATAAGTGCAAGGTGTCTAAC

AAGGCACTGCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAGGGCGGAGGAGGTCTGGCGGTGGTGGCAG

TGGTGGCGGAGGGTCAGGAGGTGGTGGAAGCATCACCTGCCCTCCACCTATGTCCG

TGGAACACGCAGACATCTGGGTCAAGAGCTACAGCTTGTACTCCCGCGAGCGCTAC

ATTTGTAACTCTGGTTTCAAGCGTAAAGCCGGCACCTCCAGCCTGACCGAGTGCGTG

TTGAACAAGGCCACCAATGTCGCCCACTGGACAACCCCAAGTCTCAAATGCATTCG

CGACCCTGCCCTGGTTCACCAACGCCCAGCGCCACCATCCACAGTAACCACTGCAG

GCGTGACCCCACAGCCAGAGAGCCTCTCCCCTTCTGGCAAAGAGCCAGCAGCTTCA

TCTCCAAGCTCAAACAACACAGCGGCCACAACAGCAGCTATTGTCCCGGGCTCCCA

GCTGATGCCTTCAAAATCACCTTCCACAGGCACCACAGAGATCAGCAGTCATGAGT

CCTCCCACGGCACCCCATCTCAGACAACAGCCAAGAACTGGGAACTCACAGCATCC

GCCTCCCACCAGCCGCCAGGTGTGTATCCACAGGGCCACAGCGACACCACTTGA

IL-15Rα-sushi+(73)-Fc (DNA sequence 4, SEQ ID NO: 13):
<u>ATGGACATGCGGGTGCCAGCCCAGCTGCTGGGCCTGTTGCTGCTGTGGTTCCCCGGC</u>

<u>TCTCGGTGC</u>ATCACCTGCCCTCCACCTATGTCCGTGGAACACGCAGACATCTGGGTC

AAGAGCTACAGCTTGTACTCCCGCGAGCGCTACATTTGTAACTCTGGTTTCAAGCGT

AAAGCCGGCACC<u>TCC</u>AGCCTGACCGAGTGCGTGTTGAACAAGGCCACCAATGTCGC

CCACTGGACAACCCCAAGTCTCAAATGCATTCGCGACCCTGCCCTGGTTCACCAACG

<u>CGGCGGAGGAGGCTCTGGGGGCGGAGGAAGC</u>GAACCTAAGTCCTCTGATAAGACC

CACACATGTCCCCCCTGCCCAGCTCCTGAGCTCTTGGGCGGACCTTCCGTGTTTCTG

TTCCCCCCAAAGCCCAAGGATACCCTTATGATCAGCAGAACACCCGAAGTTACTTG

CGTGGTCGTGGACGTTTCTCACGAAGATCCTGAAGTGAAATTCAACTGGTACGTGG

ATGGCGTGGAGGTGCACAATGCTAAGACTAAGCCCCGTGAAGAGCAGTACAACTCT

ACCTACCGGGTCGTTTCAGTGCTGACTGTTCTCCATCAGGACTGGCTCAACGGGAAG

GAGTATAAGTGCAAGGTGTCTAACAAGGCACTGCCCGCACCCATCGAGAAGACCAT

TTCTAAGGCCAAGGGTCAACCACGGGAGCCACAGGTTTACACATTGCCTCCCAGTC

GGGAGGAGATGACAAAGAATCAAGTGTCACTTACATGTCTTGTGAAGGGCTTCTAC

CCCTCAGACATCGCCGTGGAGTGGGAGAGCAACGGACAACCAGAAAACAACTACA

AGACCACACCTCCTGTGCTCGATTCAGATGGTTCCTTTTTCTTGTACAGCAAACTCA

CCGTTGACAAGAGTCGGTGGCAGCAAGGAAATGTGTTCAGCTGTTCTGTGATGCAC

GAGGCCCTGCACAACCATTATACCCAAAAATCTCTCAGCCTTTCTCCCGGCAAGTGA

C

Fc-IL-15Rα-sushi+(73) (DNA sequence 5, SEQ ID NO: 14):
<u>ATGGACATGCGGGTGCCAGCCCAGCTGCTGGGCCTGTTGCTGCTGTGGTTCCCCGGC</u>

<u>TCTCGGTGC</u>GAACCTAAGTCCTCTGATAAGACCCACACATGTCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTTCTCCATCAGGACTGGCTCAACGGGAAGGAGTATAAGTGCAAGGTGTCTAAC

AAGGCACTGCCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAG<u>GGCGGAGGAGGCTCTGGCGGTGGTGGCAG</u>

<u>TGGTGGCGGAGGGTCAGGAGGTGGTGGAAG</u>CATCACCTGCCCTCCACCTATGTCCG

TGGAACACGCAGACATCTGGGTCAAGAGCTACAGCTTGTACTCCCGCGAGCGCTAC

ATTTGTAACTCTGGTTTCAAGCGTAAAGCCGGCACC<u>TCC</u>AGCCTGACCGAGTGCGTG

TTGAACAAGGCCACCAATGTCGCCCACTGGACAACCCCAAGTCTCAAATGCATTCG

CGACCCTGCCCTGGTTCACCAACGCTGA

IL-15(L52C) (DNA sequence 6, SEQ ID NO: 15):
<u>ATGGACATGCGGGTGCCAGCCCAGCTGCTGGGCCTGTTGCTGCTGTGGTTCCCCGGC</u>

<u>TCTCGGTGC</u>AACTGGGTGAATGTAATTAGTGATTTGAAAAAAATTGAAGATCTTATT

CAATCTATGCATATTGATGCTACTTTATATACGGAAAGTGATGTTCACCCGAGTTGC

AAAGTAACAGCAATGAAGTGCTTTCTCTTGGAGTTACAAGTTATTTCA<u>TGT</u>GAGTCC

GGCGATGCAAGTATTCATGATACAGTAGAAAATCTGATCATCTTAGCAAACAACAG

TTTGTCTTCTAATGGGAATGTAACAGAATCTGGATGCAAAGAATGTGAGGAACTGG

AGGAAAAAAATATTAAAGAATTTTTGCAGAGTTTTGTACATATTGTCCAAATGTTCA

TCAACACTTCTTGA

IL-15Ra-ECD(S40C)-Fc (DNA sequence 7, SEQ ID NO: 16):
<u>ATGGACATGCGGGTGCCAGCCCAGCTGCTGGGCCTGTTGCTGCTGTGGTTCCCCGGC</u>

<u>TCTCGGTGC</u>ATCACCTGCCCTCCACCTATGTCCGTGGAACACGCAGACATCTGGGTC

AAGAGCTACAGCTTGTACTCCCGCGAGCGCTACATTTGTAACTCTGGTTTCAAGCGT

AAAGCCGGCACC<u>TGC</u>AGCCTGACCGAGTGCGTGTTGAACAAGGCCACCAATGTCGC

CCACTGGACAACCCCAAGTCTCAAATGCATTCGCGACCCTGCCCTGGTTCACCAACG

CCCAGCGCCACCATCCACAGTAACCACTGCAGGCGTGACCCCACAGCCAGAGAGCC

TCTCCCCTTCTGGCAAAGAGCCAGCAGCTTCATCTCCAAGCTCAAACAACACAGCG

GCCACAACAGCAGCTATTGTCCCGGGCTCCCAGCTGATGCCTTCAAAATCACCTTCC

ACAGGCACCACAGAGATCAGCAGTCATGAGTCCTCCCACGGCACCCCATCTCAGAC

AACAGCCAAGAACTGGGAACTCACAGCATCCGCCTCCCACCAGCCGCCAGGTGTGT

ATCCACAGGGCCACAGCGACACCACT<u>GGCGGAGGAGGCTCTGGGGGCGGAGGAAG</u>

<u>C</u>GAACCTAAGTCCTCTGATAAGACCCACACATGTCCCCCTGCCCAGCTCCTGAGCT

CTTGGGCGGACCTTCCGTGTTTCTGTTCCCCCCAAAGCCCAAGGATACCCTTATGAT

CAGCAGAACACCCGAAGTTACTTGCGTGGTCGTGGACGTTTCTCACGAAGATCCTG

AAGTGAAATTCAACTGGTACGTGGATGGCGTGGAGGTGCACAATGCTAAGACTAAG

CCCCGTGAAGAGCAGTACAACTCTACCTACCGGGTCGTTTCAGTGCTGACTGTTCTC

CATCAGGACTGGCTCAACGGGAAGGAGTATAAGTGCAAGGTGTCTAACAAGGCACT

GCCCGCACCCATCGAGAAGACCATTTCTAAGGCCAAGGGTCAACCACGGGAGCCAC

AGGTTTACACATTGCCTCCCAGTCGGGAGGAGATGACAAAGAATCAAGTGTCACTT

ACATGTCTTGTGAAGGGCTTCTACCCCTCAGACATCGCCGTGGAGTGGGAGAGCAA

CGGACAACCAGAAAACAACTACAAGACCACACCTCCTGTGCTCGATTCAGATGGTT

CCTTTTTCTTGTACAGCAAACTCACCGTTGACAAGAGTCGGTGGCAGCAAGGAAAT

GTGTTCAGCTGTTCTGTGATGCACGAGGCCCTGCACAACCATTATACCCAAAAATCT

CTCAGCCTTTCTCCCGGCAAGTGA

Fc-IL-15Rα-ECD (S40C) (DNA sequence 8, SEQ ID NO: 17):
<u>ATGGACATGCGGGTGCCAGCCCAGCTGCTGGGCCTGTTGCTGCTGTGGTTCCCCGGC</u>

<u>TCTCGGTGC</u>GAACCTAAGTCCTCTGATAAGACCCACACATGTCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTFCTCCATCAGGACTGGCTCAACGGGAAGGAGTATAAGTGCAAGGTGTCTAAC

AAGGCACTGCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAG<u>GGCGGAGGAGGCTCTGGCGGTGGTGGCAG</u>

<u>TGGTGGCGGAGGGTCAGGAGGTGGTGAAG</u>CATCACCTGCCCTCCACCTATGTCCG

TGGAACACGCAGACATCTGGGTCAAGAGCTACAGCTTGTACTCCCGCGAGCGCTAC

ATTTGTAACTCTGGTTTCAAGCGTAAAGCCGGCACC<u>TGC</u>AGCCTGACCGAGTGCGTG

TTGAACAAGGCCACCAATGTCGCCCACTGGACAACCCCAAGTCTCAAATGCATTCG

CGACCCTGCCCTGGTTCACCAACGCCCAGCGCCACCATCCACAGTAACCACTGCAG

GCGTGACCCCACAGCCAGAGAGCCTCTCCCCTTCTGGCAAAGAGCCAGCAGCTTCA

TCTCCAAGCTCAAACAACACAGCGGCCACAACAGCAGCTATTGTCCCGGGCTCCCA

GCTGATGCCTTCAAAATCACCTTCCACAGGCACCACAGAGATCAGCAGTCATGAGT

CCTCCCACGGCACCCCATCTCAGACAACAGCCAAGAACTGGGAACTCACAGCATCC

GCCTCCCACCAGCCGCCAGGTGTGTATCCACAGGGCCACAGCGACACCACTTGA

IL-15Rα-sushi+(73) (S40C)-Fc (DNA sequence 9, SEQ ID NO: 18):
<u>ATGGACATGCGGGTGCCAGCCCAGCTGCTGGGCCTGTTGCTGCTGTGGTTCCCCGGC</u>

<u>TCTCGGTGC</u>ATCACCTGCCCTCCACCTATGTCCGTGGAACACGCAGACATCTGGGTC

AAGAGCTACAGCTTGTACTCCCGCGAGCGCTACATTTGTAACTCTGGTTTCAAGCGT

AAAGCCGGCACC<u>TGC</u>AGCCTGACCGAGTGCGTGTTGAACAAGGCCACCAATGTCGC

CCACTGGACAACCCCAAGTCTCAAATGCATTCGCGACCCTGCCCTGGTTCACCAACG

CGGCGGAGGAGGCTCTGGGGGCGGAGGAAGCGAACCTAAGTCCTCTGATAAGACC

CACACATGTCCCCCTGCCCAGCTCCTGAGCTCTTGGGCGGACCTTCCGTGTTTCTG

TTCCCCCCAAAGCCCAAGGATACCCTTATGATCAGCAGAACACCCGAAGTTACTTG

CGTGGTCGTGGACGTTTCTCACGAAGATCCTGAAGTGAAATTCAACTGGTACGTGG

ATGGCGTGGAGGTGCACAATGCTAAGACTAAGCCCCGTGAAGAGCAGTACAACTCT

ACCTACCGGGTCGTTTCAGTGCTGACTGTTCTCCATCAGGACTGGCTCAACGGGAAG

GAGTATAAGTGCAAGGTGTCTAACAAGGCACTGCCCGCACCCATCGAGAAGACCAT

TTCTAAGGCCAAGGGTCAACCACGGGAGCCACAGGTTTACACATTGCCTCCCAGTC

GGGAGGAGATGACAAAGAATCAAGTGTCACTTACATGTCTTGTGAAGGGCTTCTAC

CCCTCAGACATCGCCGTGGAGTGGGAGAGCAACGGACAACCAGAAAACAACTACA

AGACCACACCTCCTGTGCTCGATTCAGATGGTTCCTTTTTCTTGTACAGCAAACTCA

CCGTTGACAAGAGTCGGTGGCAGCAAGGAAATGTGTTCAGCTGTTCTGTGATGCAC

GAGGCCCTGCACAACCATTATACCCAAAAATCTCTCAGCCTTTCTCCCGGCAAGTGA
C

Fc-IL-15Rα-sushi+(73)(S40C) (DNA sequence 10, SEQ ID NO: 19):
<u>ATGGACATGCGGGTGCCAGCCCAGCTGCTGGGCCTGTTGCTGCTGTGGTTCCCCGGC</u>

<u>TCTCGGTGC</u>GAACCTAAGTCCTCTGATAAGACCCACACATGTCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTTCTCCATCAGGACTGGCTCAACGGGAAGGAGTATAAGTGCAAGGTGTCTAAC

AAGGCACTGCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAG<u>GGCGGAGGAGGCTCTGGCGGTGGTGGCAG</u>

<u>TGGTGGCGGAGGGTCAGGAGGTGGTGGAAGC</u>ATCACCTGCCCTCCACCTATGTCCG

```
TGGAACACGCAGACATCTGGGTCAAGAGCTACAGCTTGTACTCCCGCGAGCGCTAC

ATTTGTAACTCTGGTTTCAAGCGTAAAGCCGGCACCTGCAGCCTGACCGAGTGCGTG

TTGAACAAGGCCACCAATGTCGCCCACTGGACAACCCCAAGTCTCAAATGCATTCG

CGACCCTGCCCTGGTTCACCAACGCTGA

Fc fragment: IgG1-Fc DNA (DNA sequence 11, SEQ ID NO: 20):
GAACCTAAGTCCTCTGATAAGACCCACACATGTCCCCCTGCCCAGCTCCTGAGCTC

TTGGGCGGACCTTCCGTGTTTCTGTTCCCCCCAAAGCCCAAGGATACCCTTATGATC

AGCAGAACACCCGAAGTTACTTGCGTGGTCGTGGACGTTTCTCACGAAGATCCTGA

AGTGAAATTCAACTGGTACGTGGATGGCGTGGAGGTGCACAATGCTAAGACTAAGC

CCCGTGAAGAGCAGTACAACTCTACCTACCGGGTCGTTTCAGTGCTGACTGTTCTCC

ATCAGGACTGGCTCAACGGGAAGGAGTATAAGTGCAAGGTGTCTAACAAGGCACTG

CCCGCACCCATCGAGAAGACCATTTCTAAGGCCAAGGGTCAACCACGGGAGCCACA

GGTTTACACATTGCCTCCCAGTCGGGAGGAGATGACAAAGAATCAAGTGTCACTTA

CATGTCTTGTGAAGGGCTTCTACCCCTCAGACATCGCCGTGGAGTGGGAGAGCAAC

GGACAACCAGAAAACAACTACAAGACCACACCTCCTGTGCTCGATTCAGATGGTTC

CTTTTTCTTGTACAGCAAACTCACCGTTGACAAGAGTCGGTGGCAGCAAGGAAATG

TGTTCAGCTGTTCTGTGATGCACGAGGCCCTGCACAACCATTATACCCAAAAATCTC

TCAGCCTTTCTCCCGGCAAG
```

Example 3. Characteristics of IL-15 Protein Complex

The IL-15 protein complex provided in the present invention consists of a soluble fusion protein (I) and a soluble fusion protein (II), wherein the soluble fusion protein (I) comprises an IL-15 polypeptide covalently linked to a biologically active polypeptide or a functional fragment thereof. The soluble fusion protein (II) comprises an IL-15R alpha polypeptide covalently linked to a biologically active polypeptide or a functional fragment thereof, wherein the soluble fusion protein (I) or the soluble fusion protein (II) possesses Cys resulting from one or more amino acid mutation sites, and a disulfide bond is formed by the pairing of the corresponding Cys present in the soluble fusion protein (II) and the soluble fusion protein (I).

In the present invention, a stable protein complex with obvious anti-tumor activity and prolonged in vivo half-life was constructed by a gene engineering method, and the complex molecule comprises an Fc fusion protein molecule of IL-15 or a derivative thereof and IL-15Rα or a derivative thereof.

The fusion protein molecule has the following features:
1) The fusion protein comprises two major molecular moieties, one of which is a molecule having IL-15 biological activity and the other is an Fc fusion molecule having IL-15Rα or a functional fragment thereof;
2) The molecular moiety having IL-15 bioactivity has cysteine mutations at one or more amino acid sites on the basis of wild-type IL-15 or IL-15 functional mutants, and these cysteine mutation sites can be paired with the corresponding cysteine mutation sites on IL-15Rα or its functional fragment to form a disulfide bond;
3) The Fc fusion molecule moiety having an IL-15Rα or functional fragment has cysteine mutations at one or more amino acid sites on the basis of the entire extracellular domain fragment of IL-15Rα or an IL-15Rα functional fragment containing a shortened form of the sushi domain. These cysteines can be paired with the corresponding cysteine mutation sites on IL-15 or a functional mutant thereof to form a disulfide bond;
4) The fusion protein can be stably expressed by co-transfecting or constructing a single cell line with two plasmids, and a single molecule can be obtained by conventional separation methods.

IL-15 used in the examples of the present invention refers to human interleukin 15 mature molecules (SEQ ID NO: 1) or variants thereof. The IL-15Rα ECD used in the examples of the present invention refers to human interleukin 15 receptor alpha extracellular domain fragment (SEQ ID NO: 3). The variant thereof is preferably a shortened version thereof, such as IL-15Rα-sushi+(SEQ ID NO: 4). The Fc fragment portion used in the examples of the present invention is an Fc fragment of human antibody IgG1, IgG2, IgG3, or IgG4, or a variant thereof, preferably an Fc fragment of human IgG1, more preferably SEQ ID NO: 9.

In the present invention, IL-15Rα or a derivative thereof is fused to an Fc fragment or Fc variant through a linker peptide to form a soluble fusion protein (II), in which the order of attachment of each protein component is not limited. The linker peptide can be a soft linker commonly used in the art, and preferably is (GGGGS) n, where n can be from 1 to 10, preferably from 1 to 5, and most preferably 2. In addition to binding IL-15 to IL-15R alpha, the soluble fusion protein (II) and soluble fusion protein (I) can also be combined through a disulfide bond formed via pairing cysteine mutation sites. The stability of the molecule can be increased by the latter.

Related protein sequences are as follows:

IL-15 (SEQ ID NO: 1): (human Interleukin 15 amino acid sequence, and also the reference IL-15 sequence)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

IL-15(L52C) (SEQ ID NO: 2): (human Interleukin 15 amino acid sequence with a mutation L52C on position 52)
NWVNVISDLKKIEDLIQSMHIDATLYTESDVHPSCKVTAMKCFLLELQVI

SCESGDASIHDTVENLIILANNSLSSNGNVTESGCKECEELEEKNIKEFL

QSFVHIVQMFINTS

IL-15Rα-ECD (SEQ ID NO: 3): (The amino acid sequence of the extracellular domain of human interleukin 15 receptor alpha)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTT

IL-15Rα-sushi+ (SEQ ID NO: 4): (The truncated form of the human interleukin 15 receptor fragment, containing 73 amino acids)
ITCPPPMSVEHADIWVKSYSLYSRERYICNSGFKRKAGTSSLTECVLNKA

TNVAHWTTPSLKCIRDPALVHQR

IL-15Rα-ECD (S40C)-Fc (SEQ ID NO: 5): (fusion polypeptide of IL-15Rα extracellular domain fused to Fc, which contains an S40C mutation site)
ITCPPPMSVEHADIWVKSYSLYSRERYICNSGFKRKAGTCSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTTGGGGSGGGGSEPKSSDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

Fc-IL-15Rα-ECD (S40C) (SEQ ID NO: 6): (fusion polypeptide of Fc fused to IL15Rα extracellular region, which contains an S40C mutation)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKGGGGSGGGGSITCPPPMS

VEHADIWVKSYSLYSRERYICNSGFKRKAGTCSLTECVLNKATNVAHWTT

PSLKCIRDPALVHQRPAPPSTVTTAGVTPQPESLSPSGKEPAASSPSSNN

TAATTAAIVPGSQLMPSKSPSTGTTEISSHESSHGTPSQTTAKNWELTAS

ASHQPPGVYPQGHSDTT

IL-15Rα-Sushi+ (S40C)-Fc (SEQ ID NO: 7): (A truncated form of human interleukin 15 receptor a containing the sushi domain fused to the Fc via a linker, wherein sushi⁺ contains an S40C mutation and sushi⁺ is located at the N-terminus)
ITCPPPMSVEHADIWVKSYSLYSRERYICNSGFKRKAGTCSLTECVLNKA

TNVAHWTTPSLKCIRDPALVHQRGGGGSGGGGSEPKSSDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK

Fc-IL-15Rα-sushi+ (S40C)(SEQ ID NO: 8): (A truncated form of human interleukin 15 receptor containing the sushi domain fused to the Fc via a linker, wherein sushi⁺ contains an S40C mutation and sushi⁺ is located at the C-terminus)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKGGGGSGGGGSITCPPPMS

VEHADIWVKSYSLYSRERYICNSGFKRKAGTCSLTECVLNKATNVAHWTT

PSLKCIRDPALVHQR

Fc Fragment, IgG 1-Fc (Protein)
(SEQ ID NO: 9)
EPKSSDKTHTCPPCPAPELLGGPSVFLFPPKPKDILMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Figure 7:
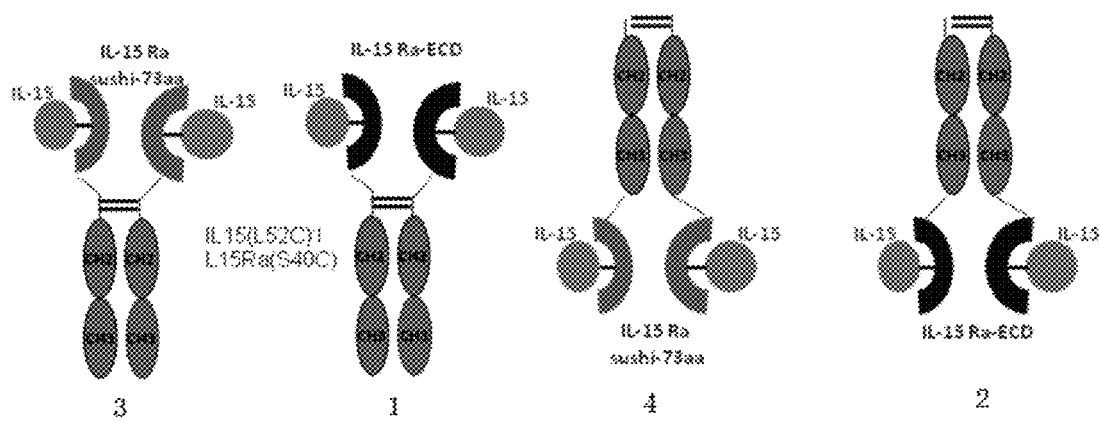
FIG. 7 shows a structure diagram of protein complexes 1, 2, 3, 4 of the present invention.

In the experiments, the molecules to be tested were numbered as follows: protein complexes 1, 2, 3, and 4, wherein protein complex 1 was obtained by co-expression of SEQ ID NO: 2 and SEQ ID NO: 5; protein complex 2 was obtained by co-expression of SEQ ID NO: 2 and SEQ ID NO: 6; protein complex 3 was obtained by co-expression of SEQ ID NO: 2 and SEQ ID NO: 7; And protein complex 4 was obtained by co-expression of SEQ ID NO:2 and SEQ ID NO:8. A schematic diagram is shown in FIG. 7. The stability of the complex molecule was increased by increasing the formation of a disulfide bond by pairing the cysteine mutation sites.

The list of protein complexes is as follows:

| NO. | Sequence composition and description |
|---|---|
| 1 | Obtained by IL-15 (L52C) (SEQ ID NO: 2) and IL-15Rα-ECD (S40C)-Fc (SEQ ID NO: 5) co-expression |
| 2 | Obtained by IL-15(L52C) (SEQ ID NO: 2) and Fc-IL-15Rα-ECD (S40C) (SEQ ID NO: 6) co-expression |
| 3 | Obtained by IL-15(L52C) (SEQ ID NO: 2) and IL-15Rα-Sushi + (S40C)-Fc (SEQ ID NO: 7) co-expression |
| 4 | Obtained by IL-15(L52C)(SEQ ID NO: 2) and Fc-IL-15Rα-sushi + (S40C) (SEQ ID NO: 8) co-expression |

Example 4. Obtaining the IL-15 Protein Complex

1. Protein Expression

IL-15/IL-15Rα protein was transiently transfected and expressed by using FreeStyle 293 cells (GIBCO, Cat #R79007). FreeStyle 293 cells were suspension cultured in Freestyle 293 expression medium (GIBCO, Cat #12338018), and supplemented with Ultra Low IgG Fetal Bovine Serum (ultra low immunoglobulins FBS, GIBCO, Cat #16250078) at a final concentration of 1%. IL-15/IL-15Rα expression plasmids and transfection reagent PEI (Polysciences, Cat #239662) were prepared, and the two plasmids of IL-15 and IL-15Rα were co-transfected at a ratio ranging from 1:1 to 9:1, wherein the total amount of plasmids was 100 ug/100 ml cells, the ratio of plasmid to PEI was 1:2 by mass. Cell density on the day of transfection was $1\times10^6$/ml. 1L of FreeStyle 293 cells was prepared to be transfected. 50 ml of Opti-MEM (GIBCO, Cat #11058021) medium was mixed with the plasmid, kept still for 5 min and filtered. Another 50 ml of Opti-MEM medium was mixed with PEI, kept still for 5 min and filtered. The plasmid was mixed with PEI and kept still for 15 min. The mixture of plasmid and PEI was slowly added to the cells and cultured in a shaking incubator at 130 rpm at 37° C., 8% $CO_2$. Five (5) days later, the supernatant was collected by centrifugation for protein purification.

2. Protein Purification

Affinity Chromatography for IL-15 Fusion Protein:

Supernatant was collected from cell culture after high speed centrifugation and subjected to affinity chromatography by using a Protein A column from GE. The equilibration buffer used in chromatography was 1×PBS (pH7.4). After cell supernatant was loaded and bound, it was washed with PBS until UV returned to baseline, and then the target protein was eluted with elution buffer (acidity, pH2.5-5). The pH was adjusted to neutral with Tris, and the target protein was stored.

Ion Exchange Chromatography for IL-15 Fusion Protein:

The pH of the product obtained during the affinity chromatography was adjusted to be 1-2 pH units lower or higher than pI. Then the sample was appropriately diluted to control the conductivity of the sample to less than 5 ms/cm. NaCl-gradient elution under corresponding pH conditions was performed by utilizing a suitable buffer corresponding to the pH, such as phosphate buffer, acetate buffer, and others, by utilizing conventional ion-exchange column chromatography methods in the art such as cation exchange or anion exchange. The target proteins corresponding to different absorption peaks were collected by using SDS-PAGE and stored.

Size Exclusion Chromatography for IL-15 Fusion Protein:

The product obtained during the ion exchange chromatography was concentrated by ultrafiltration and loaded for size exclusion chromatography, such as by using GE Superdex200 gel to remove possible polymer and other components, in order to obtain the desired product with high purity. Purity of the obtained protein was detected by SDS-PAGE and SEC-HPLC. Protein concentration was determined by UV spectrophotometry.

TEST EXAMPLES

Test Example 1. PBMC Proliferation Assay In Vitro

Fresh PBMCs (human peripheral blood mononuclear cells, Shanghai Blood Center) were cultured in RPMI1640 medium (Thermo Fisher Chemical Products Co., Ltd (Beijing), Cat No. SH30809.01B) containing 10% FBS, centrifuged and resuspended to a cell density of $5\times10^5$ cells/ml. 90 μl were added into each well of a 96-well plate. Samples were diluted at certain multiples to different concentrations with PBS. 10 μl were added into each well of a 96-well plate, and cultured in the incubator at 37° C., 5% $CO_2$ for 48 hours. Thereafter, 50 μl were taken for detection of cell proliferation with CellTiter-Glo® Luminescent Cell Viability Assay kit.

TABLE 5

Detection results of activity of protein complexes 1 and 3 of the present invention in PBMC proliferation assay in vitro

| Sample | EC50 (ng/ml) | relative activity of the cells |
|---|---|---|
| IL-15 | 3.115 | 100 |
| 1 | 0.634 | 491 |
| 3 | 0.047 | 6627 |

Table 5 shows the detection results of activity of protein complexes 1 and 3 of the present invention versus control IL-15 in a PBMC proliferation assay in vitro, which indicate that the protein complexes 1 and 3 of the present application significantly improved the proliferation activity of PBMC compared to control IL-15. In this experiment, the activity stimulated by protein complex 1 was increased by about 5 times, whereas the activity stimulated by protein complex 3 was improved by about 66 folds.

Test Example 2. Mole Cell Proliferation Assay In Vitro

1. Main Materials

Mo7e (human megakaryocyte leukemia cell line) purchased from Peking Union Medical College;

IL-15 purchased from Novoprotein, Cat No. C016, IL-15 analog was obtained from in-house preparation;

Cell Counting Kit-8 (CCK-8) purchased from WST, Cat No. EX660;

GM-CSF purchased from NOVOProtein, Cat No. CC79.

2. Procedures

1) Mo7e was cultured in modified RPMI-1640 medium (containing 2.05 mM L-glutamine, 10% FBS and 15 ng/ml GM-CSF) in the incubator at 37° C. (5% $CO_2$);

2) Mo7e cells in good condition were centrifuged at room temperature, 150×g for 5 min. The supernatant was discarded;

3) The cell pellet was washed with GM-CSF-free medium twice and then counted;

4) Cell concentration was adjusted and plated in a 96-well plate with a cell number of $2\times10^4$ per well and a volume of 90 μl (GM-CSF-free), kept in the cell incubator for culture;

5) IL-15 and its analog were 4-times diluted with PBS, 10 μl/well was added to the cell culture system after 2 hours of incubation of cells in 96-well plates. Each concentration was repeated in triplicate, blank wells (added with only PBS) were used as control;

6) Cell plates were cultured in the incubator for 3 days;

7) All test wells were added with 10 µl of CCK-8, and incubated in the incubator for 3 hours;

8) Absorbance at 450 nm (OD450) was detected.

TABLE 6

Results of protein complexs 1-4 in Mo7e cell proliferation assay in vitro

| Sample | EC50 (nM)-Mo7e | relative activity of the cells |
|---|---|---|
| IL-15 | 15.5 | 100 |
| 1 | 0.42 | 3690 |
| 2 | 1.21 | 1281 |
| 3 | 0.07 | 22142 |
| 4 | 0.09 | 17222 |

Table 6 shows the comparison of protein complexes 1-4 to control IL-15 in a Mo7e cell proliferation assay in vitro, which indicates that the protein complexes 1-4 significantly improved the proliferation activity compared to control IL-15, and that the proliferation activity stimulated by complexes 3 and 4 was significantly higher than that stimulated by protein complexes 1 and 2.

Test Example 3. Mouse Lung Metastasis Model

1. Animal Test Procedures

Thirty-two (32) of C57BL/6 mice (SPF, Shanghai Super B&K Laboratory Animal Corp. Ltd.) were divided into 4 groups, each group having 8 mice. $1.5 \times 10^5$ of B16F10 cells were intravenously injected into the mice via the tail-vein (Cell Resource Center, Shanghai Institutes for Biological Sciences, Chinese Academy of Sciences, TCM36). PBS, 2 µg of IL-15 or 5 µg or 15 µg of protein complex 3 was intraperitoneally injected into the mice on day 1. Weighing once every 2-3 days, one mouse from each group was killed on day 14, and the lung metastasis was observed. All mice were sacrificed on day 16. Lungs of all mice were removed and weighed, the black lung lumps observed and photographed, and then the lung was fixed in formaldehyde and the number of black lumps was counted.

2. Results

Lungs of mice in the PBS group showed a large number of metastatic melanoma growing (73±43). Lungs of the IL-15 group showed a large number of melanoma lumps (65±29), about 90% of that in the PBS group. Lungs of protein complex 3-5 µg group showed a partial metastasis of melanoma lumps (30±16), about 41% of that in PBS group. Lungs of protein complex 3-15 µg groups showed a partial metastasis of melanoma lumps (24±13), about 33% of that in the PBS group.

Figure 8:
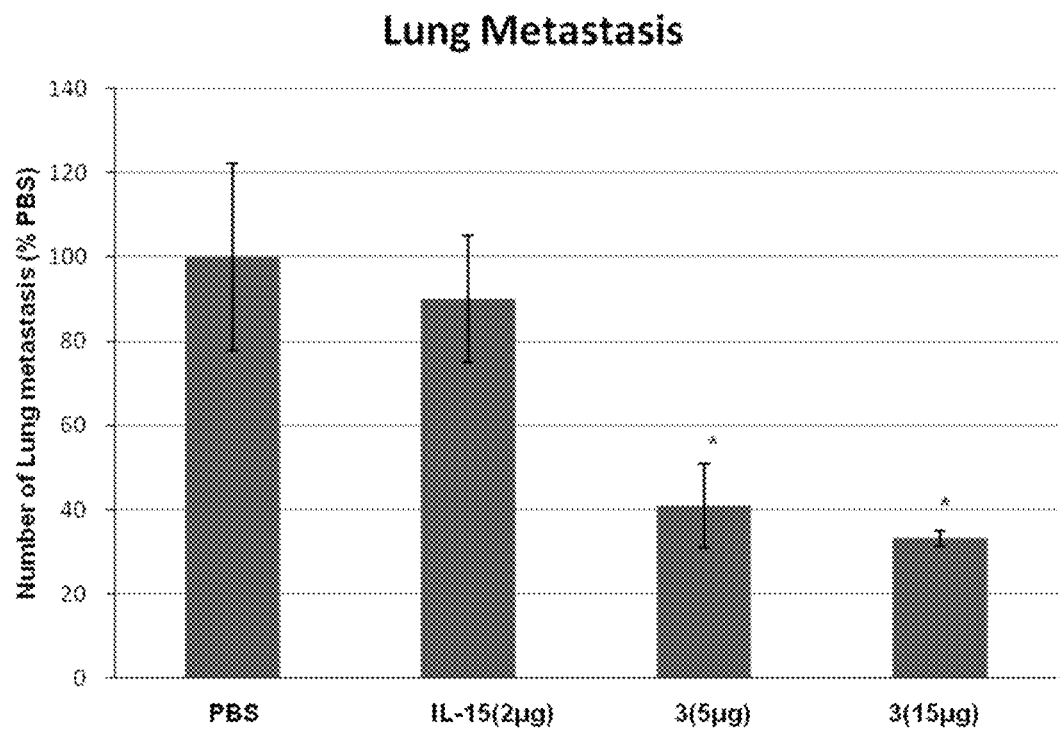
FIG. 8 shows the effect of the protein complex of the present invention on lung metastatic tumors in mice; "*" in the figure represents p<0.05, vs PBS.

In the B16F10 mouse model, the efficacy of protein complex 3 was significantly superior to that of IL-15, as shown in FIG. 8.

Figure 9:
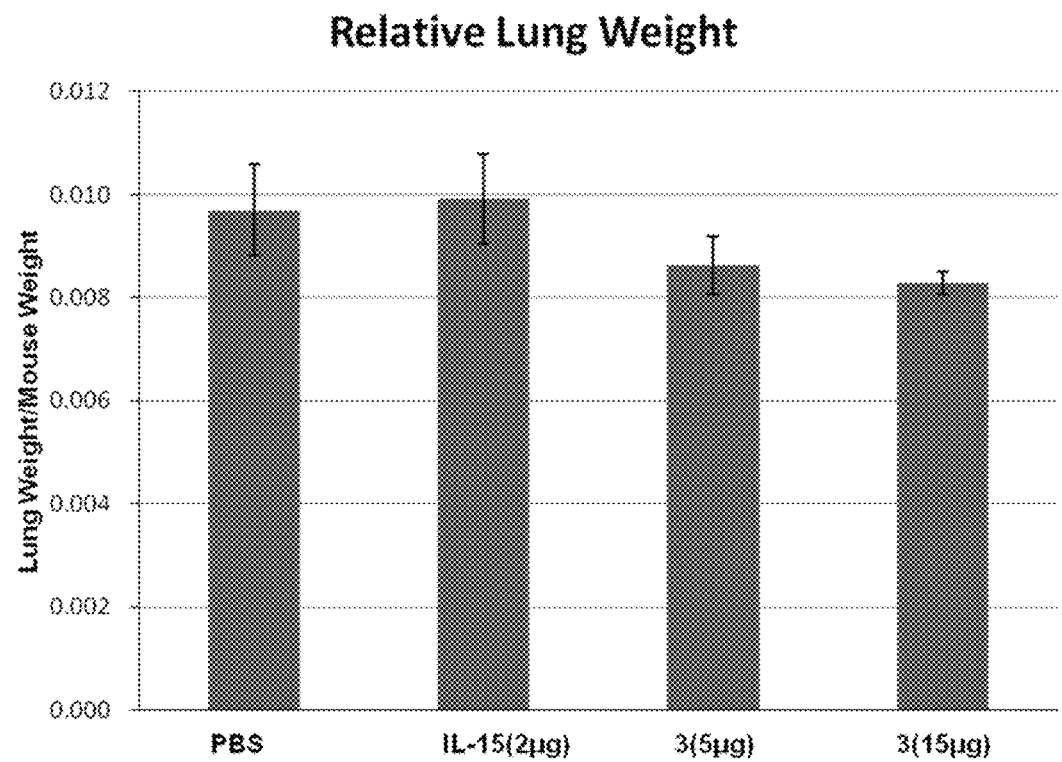
FIG. 9 shows the effect of the protein complex on the relative lung weight (lung weight/body weight) of mice.

The relative lung weight in the PBS group was significantly higher than that in protein complex 3 group, as shown in FIG. 9.

Figure 10:
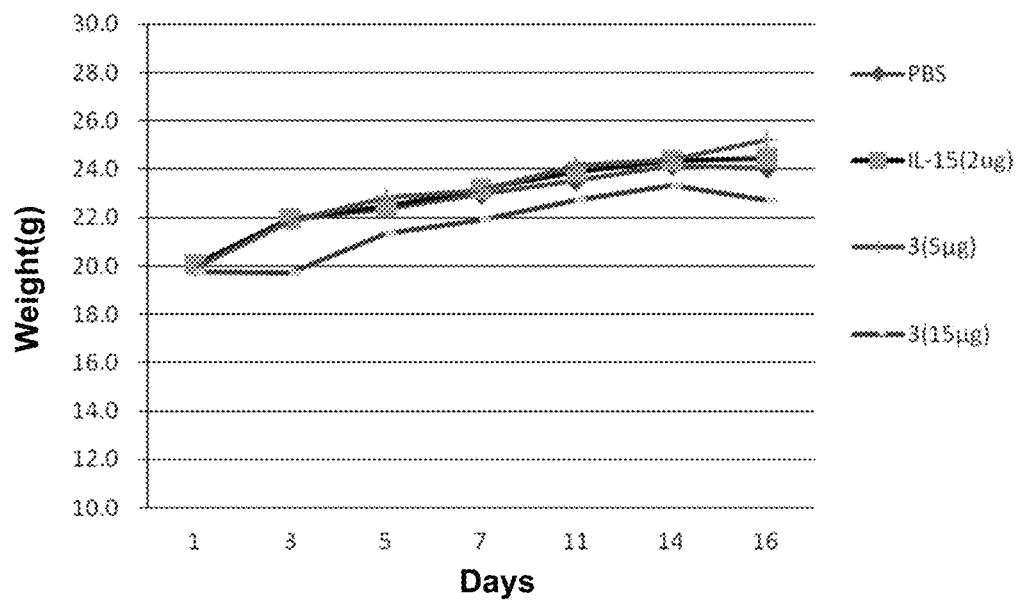
FIG. 10 shows the effect of the protein complex on the body weight of mice.
Figure 11:
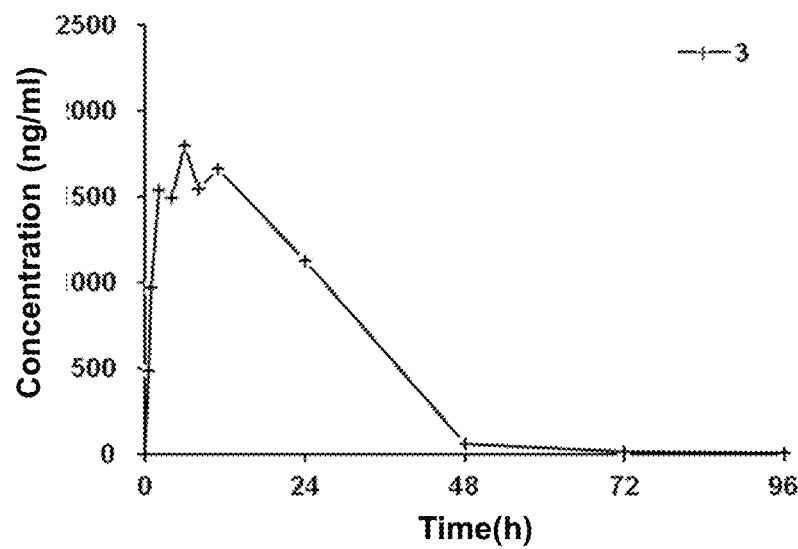
FIG. 11 shows the half-life of protein complex 3 in rat.

No significant decrease in body weight was observed in each group during the administration, suggesting that the administration dosage does not have significant toxicity, as shown in FIG. 10.

In another B16F10 mouse model experiment with another dosing group, we observed significant anti-tumor activity when the dose of protein complex 3 was reduced to 0.5 µg/mouse, whereas no obvious abnormal symptoms was observed when the maximum tolerated dose was 30 µg/mouse.

In summary, protein complex 3 can inhibit the metastasis of B16F10 cells in mice lungs, and has a dose-dependent effect and a good safety window.

Test Example 4. Mouse Subcutaneous Tumor Model

1. Animal Test Procedures 1.1 Mice were Adapted to the Laboratory Environment for 5 Days.

1.2 Tumor Cells Transplantation

C57BL/6 mice (SPF, Shanghai Xi Puer Bei Kai Experimental Animal Co., Ltd.) were inoculated subcutaneously in the right rib with B16F10 cells ($5 \times 10^6$/mouse). Tumors grew for 7 days. When the volume of the tumor grew to 160±40 mm$^3$, animals were randomly divided (d0) into 4 groups, each group of 7 mice.

1.3 Administration Dosage and Method

Each group was intraperitoneally injected with test drug once on day 1 and day 5, totally twice, with PBS, or IL-15(2 µg), or protein complex 3(5 µg), or protein complex 3(15 µg). Mice were measured for tumor volume and body weight every 2 days, and data was recorded.

1.4 Statistics

Excel statistical software: mean value was calculated as avg; SD was calculated as STDEV; SEM was calculated as STDEV/SQRT; P value between different groups was calculated as TTEST.

Tumor volume ($V$) was calculated as: $V=\frac{1}{2} \times L_{length} \times L_{short}^2$ Relative volume $(RTV)=V_T/V_0$ Tumor Inhibition Rate $(\%)=(C_{RTV}-T_{RTV})/C_{RTV}(\%)$ $V_0$ and $V_T$ represent the tumor volume at the beginning of the experiment and at the end of the experiment, respectively. $C_{RTV}$ and $T_{RTV}$ represent blank control group (PBS) and relative tumor volume in the test group at the end of the experiment, respectively.

2. Results

Since the transplanted B16F10 cell tumors grew very rapidly, the experiment was stopped on day 9. The growth inhibition effect of IL-15 protein on B16F10 tumor is shown in Table 1. After one-dose administration on days 1 and 5, respectively, IL-15 did not inhibit the growth of transplanted B16F10 cell tumors on day 9. However, the inhibitory rate in the protein complex 3-5 µg group and 3-15 µg group was 30% and 73%, respectively, wherein the protein complex 3-15 µg group significantly inhibited the tumor growth.

In conclusion, the protein complex 3 has an effect on inhibiting the growth of B16F10 xenografts in this study, and has obvious dose-dependent effects, see Table 7.

TABLE 7

| | | | Mean tumor volume (mm3) | | Mean tumor volume (mm3) | | Relative tumor volume | | % Inhibition | |
|---|---|---|---|---|---|---|---|---|---|---|
| Group | Administration | Pathway | D1 | SEM | D9 | SEM | D28 | SEM | Rate D28 | p (vs blank) |
| PBS | d1/5 | i.p. | 162.39 | 16.32 | 2703.46 | 393.15 | 16.32 | 2.18 | | |
| IL-15-2 μg | d1/5 | i.p. | 161.74 | 16.64 | 3219.01 | 644.69 | 18.32 | 2.99 | −12% | 0.60 |
| 3-5 μg | d1/5 | i.p. | 168.26 | 19.22 | 1892.20 | 315.12 | 11.47 | 1.58 | 30%** | 0.10 |
| 3-15 μg | d1/5 | i p | 168.30 | 19.17 | 824.58 | 170.63 | 4.48 | 0.61 | 73%** | 0.00 |

**p < 0.01, vs PBS

Text Example 5. Determination of the Metabolic Half-Life of the Protein Complexes 1. Animal Test Procedures The SD rats (n=2, provided by Sipur-Bikai Experimental Animal Co., Ltd.) were administered via intraperitoneal injection with a dose of 188 μg/kg in a volume of 5 ml after fasting overnight. 0.2 ml blood samples were taken through the rat retro-orbital plexus before and after administration and at 0.5 h, 1 h, 2 h, 4 h, 6 h, 8 h, 11 h, 24 h, 48 h, 72 h and 96 h. The blood samples were collected in a tube and kept in the tube for 30 min at 4° C., then centrifuged at 3500 rpm for 10 min and the serum was isolated. Stored at −80° C. The rats were fed 2 h after administration.

2. Results

Protein complex 3 in rat serum was captured by an ELISA plate coated with anti-IL-15 antibody. Anti-human IgG Fc antibody was used to detect the concentration curve, and the measured half-life in vivo of protein complex 3 in rat was about 13.7 h (FIG. 10). It is reported that the half-life in vivo of IL-15 is less than 1 h (*J Immunol* 2006; 177:6072-6080), which indicates that the protein complex 3 has a significantly prolonged half-life in vivo.

The invention claimed is:

1. An IL-15 protein complex comprising a soluble fusion protein (I) and a soluble fusion protein (II), wherein:
   the soluble fusion protein (I) comprises an IL-15 polypeptide; and the soluble fusion protein (II) comprises an IL-15Rα polypeptide;
   wherein the soluble fusion protein (I) comprises an amino acid Cys substitution at a position corresponding to residue Q48, V49, L52 or E53 of the IL-15 polypeptide having the amino acid sequence of SEQ ID NO: 1, and the soluble fusion protein (II) comprises an amino acid Cys substitution at a position corresponding to residue G38, S40 or L42 of the IL-15Rα polypeptide having the amino acid sequence of SEQ ID NO: 4, and a disulfide bond is formed by Cys residues of the soluble fusion protein (II) and the soluble fusion protein (I).

2. The IL-15 protein complex according to claim 1, wherein at least one of the soluble fusion protein (I) and soluble fusion protein (II) is covalently linked to an Fc fragment.

3. The IL-15 protein complex according to claim 1, wherein the sequence of the soluble fusion protein (I) comprises SEQ ID NO: 2.

4. The IL-15 protein complex according to claim 1, wherein the soluble fusion protein (II) is obtained by recombination of the IL-15Rα polypeptide and an Fc fragment.

5. The IL-15 protein complex according to claim 1, wherein the sequence of the soluble fusion protein (II) comprises a sequence selected from the group consisting of SEQ ID NO: 5, SEQ ID NO: 6, SEQ ID NO: 7 and SEQ ID NO: 8.

6. The IL-15 protein complex according to claim 1, being selected from the following combinations of a soluble fusion protein (I) and a soluble fusion protein (II):

| No. | soluble fusion protein (I) | soluble fusion protein (II) |
| --- | --- | --- |
| 1 | IL-15(L52C)(SEQ ID NO: 2) | IL-15Rα-ECD(S40C)-Fc (SEQ ID NO: 5) |
| 2 | IL-15(L52C)(SEQ ID NO: 2) | Fc-IL-15Rα-ECD(S40C)(SEQ ID NO: 6) |
| 3 | IL-15(L52C)(SEQ ID NO: 2) | IL-15Rα-sushi + (S40C)-Fc(SEQ ID NO: 7) |
| 4 | IL-15(L52C)(SEQ ID NO: 2) | Fc-IL-15Rα-sushi + (S40C)(SEQ ID NO: 8). |

7. A pharmaceutical composition comprising the IL-15 protein complex according to claim 1, and a pharmaceutically acceptable excipient, diluent or carrier.

8. The IL-15 protein complex according to claim 1, wherein the soluble fusion protein (I) comprises an amino acid Cys substitution at the position corresponding to residue L52 or E53 of the IL-15 polypeptide having the amino acid sequence of SEQ ID NO: 1; and the soluble fusion protein (II) comprises an amino acid Cys substitution at the position corresponding to residue A37, G38 or S40 of the IL-15Rα polypeptide having the amino acid sequence of SEQ ID NO: 3 or SEQ ID NO: 4.

9. The IL-15 protein complex according to claim 1, wherein the soluble fusion protein (I) comprises an amino acid Cys substitution at the position corresponding to residue L52 of the IL-15 polypeptide having the amino acid sequence of SEQ ID NO: 1; and wherein the soluble fusion protein (II) comprises an amino acid Cys substitution at the position corresponding to residue S40 of the IL-15Rα polypeptide having the amino acid sequence of SEQ ID NO: 3 or SEQ ID NO: 4.

10. The IL-15 protein complex according to claim 4, wherein the IL-15Rα polypeptide is attached to the N-terminus of the Fc fragment and wherein the Fc fragment comprises the amino acid sequence of SEQ ID NO: 9.

* * * * *